US011376222B2

(12) United States Patent
Van Der Beek et al.

(10) Patent No.: US 11,376,222 B2
(45) Date of Patent: Jul. 5, 2022

(54) LIPID COMPOSITION FOR IMPROVING BODY COMPOSITION DURING CATCH-UP GROWTH

(71) Applicant: N.V. Nutricia, Zoetermeer (NL)

(72) Inventors: Eline Marleen Van Der Beek, Utrecht (NL); Marieke Abrahamse-Berkeveld, Utrecht (NL); Inga Christiane Teller, Utrecht (NL)

(73) Assignee: N.V. NUTRICIA, Zoetermeer (NL)

( * ) Notice: Subject to any disclaimer, the term of this patent is extended or adjusted under 35 U.S.C. 154(b) by 127 days.

(21) Appl. No.: 16/845,972

(22) Filed: Apr. 10, 2020

(65) Prior Publication Data

US 2020/0306189 A1  Oct. 1, 2020

Related U.S. Application Data

(62) Division of application No. 15/033,471, filed as application No. PCT/NL2014/050761 on Nov. 3, 2014, now abandoned.

(30) Foreign Application Priority Data

Nov. 1, 2013 (EP) ..................................... 13191300

(51) Int. Cl.
| | | |
|---|---|---|
| *A61K 9/16* | (2006.01) | |
| *A61K 31/20* | (2006.01) | |
| *A23L 33/115* | (2016.01) | |
| *A23L 33/17* | (2016.01) | |
| *A23L 33/00* | (2016.01) | |
| *A61K 31/661* | (2006.01) | |

(52) U.S. Cl.
CPC ............ *A61K 9/167* (2013.01); *A23L 33/115* (2016.08); *A23L 33/17* (2016.08); *A23L 33/40* (2016.08); *A61K 31/20* (2013.01); *A61K 31/661* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 5,709,888 A | | 1/1998 | Gil et al. |
| 7,776,332 B1* | | 8/2010 | Kuslys ................. A23L 33/40 424/157.1 |
| 8,883,219 B2 | | 11/2014 | Van Der Beek et al. |
| 9,320,294 B2 | | 4/2016 | Van Baalen et al. |
| 9,345,259 B2 | | 5/2016 | Van Der Beek et al. |
| 9,532,966 B2 | | 1/2017 | Van Der Beek et al. |
| 9,649,286 B2 | | 5/2017 | Van Der Beek et al. |
| 2002/0004527 A1 | | 1/2002 | Auestad et al. |
| 2003/0104078 A1 | | 6/2003 | Barrett-Reis et al. |
| 2004/0022922 A1 | | 2/2004 | Rutenberg |
| 2004/0062820 A1 | | 4/2004 | Lasekan et al. |
| 2005/0037089 A1 | | 2/2005 | Jobbins |
| 2005/0214392 A1 | | 9/2005 | McPeak et al. |
| 2006/0188614 A1 | | 8/2006 | Shapira |
| 2006/0210697 A1 | | 9/2006 | Mower |
| 2007/0073193 A1 | | 3/2007 | Park |
| 2007/0073194 A1 | | 3/2007 | Chen et al. |
| 2008/0003330 A1 | | 1/2008 | Rueda et al. |
| 2008/0064656 A1 | | 3/2008 | Van Tol |
| 2008/0292724 A1 | | 11/2008 | Hageman et al. |
| 2009/0011075 A1 | | 1/2009 | Shulman et al. |
| 2009/0035437 A1* | | 2/2009 | Bovetto ............... A23C 21/026 426/588 |
| 2009/0136615 A1 | | 5/2009 | Speelmans et al. |
| 2009/0186803 A1 | | 7/2009 | Zwijsen et al. |
| 2011/0206743 A1 | | 8/2011 | Van Baalen et al. |
| 2011/0217411 A1 | | 9/2011 | Van Der Beek et al. |
| 2011/0294757 A1 | | 12/2011 | Shulman et al. |
| 2011/0300204 A1 | | 12/2011 | Van Der Beek et al. |
| 2011/0300225 A1 | | 12/2011 | Van Der Beek et al. |
| 2012/0035274 A1 | | 2/2012 | Park |
| 2012/0039852 A1 | | 2/2012 | Darimont-Nicolau et al. |
| 2012/0148588 A1 | | 6/2012 | Knopf et al. |
| 2013/0052297 A1 | | 2/2013 | Van De Heijning et al. |
| 2013/0071446 A1 | | 3/2013 | Van Der Beek et al. |

(Continued)

FOREIGN PATENT DOCUMENTS

| | | |
|---|---|---|
| EP | 0 333 288 A1 | 9/1989 |
| EP | 1 252 824 A2 | 10/2002 |
| EP | 1 800 675 A1 | 6/2007 |
| EP | 2 305 049 | 4/2011 |
| EP | 2 465 359 | 6/2012 |
| EP | 2 583 562 A1 | 4/2013 |
| EP | 2 825 062 B1 | 1/2015 |
| JP | 2001-158736 | 6/2001 |
| SU | 1084006 A | 4/1984 |

(Continued)

OTHER PUBLICATIONS

"Obesity Prevention Source: Prenatal and Early Life Influences", Harvard University, retrieved Jul. 11, 2016 from URL: https://www.hsph.harvard.edu/obesity-prevention-source/obesity-causes/prenatal-postnatal . . . (11 pages).

(Continued)

*Primary Examiner* — Dominic Lazaro

(74) *Attorney, Agent, or Firm* — Foley & Lardner LLP

(57) ABSTRACT

The invention relates to nutritional compositions comprising specifically designed lipid globules that are especially suited for preterm infants, small for gestational age infants and infants with retarded growth due to physical or mental stress after birth, for promoting catch-up growth and/or for use in improving body composition, improving adipose tissue distribution, decreasing visceral adipose tissue based on body weight and/or on total adipose tissue, and/or decreasing the ratio visceral adipose tissue to subcutaneous adipose tissue, in such infants, and/or providing nutrition to such infants.

11 Claims, No Drawings

(56) References Cited

U.S. PATENT DOCUMENTS

| | | |
|---|---|---|
| 2013/0096087 A1 | 4/2013 | Van Der Beek et al. |
| 2014/0093554 A1 | 4/2014 | Van Der Beek et al. |
| 2014/0162223 A1 | 6/2014 | Saavedra et al. |
| 2015/0306117 A1 | 10/2015 | Van Der Beek et al. |
| 2016/0015068 A1 | 1/2016 | Ao et al. |
| 2016/0205983 A1 | 7/2016 | Van Baalen et al. |
| 2016/0219915 A1 | 8/2016 | Van Der Beek et al. |

FOREIGN PATENT DOCUMENTS

| | | | |
|---|---|---|---|
| WO | WO-98/44917 A1 | 10/1998 | |
| WO | WO-03/005836 A2 | 1/2003 | |
| WO | WO-2005/007373 A1 | 1/2005 | |
| WO | WO-2005/051091 A1 | 6/2005 | |
| WO | WO-2005/051092 A2 | 6/2005 | |
| WO | WO-2005/063050 A1 | 7/2005 | |
| WO | WO-2006/052134 A2 | 5/2006 | |
| WO | WO-2006/094995 A1 | 9/2006 | |
| WO | WO-2006/114790 A2 | 11/2006 | |
| WO | WO-2007/039596 A1 | 4/2007 | |
| WO | WO-2007/073192 A2 | 6/2007 | |
| WO | WO-2007/073193 A2 | 6/2007 | |
| WO | WO-2007/073194 A2 | 6/2007 | |
| WO | WO-2007/097523 A2 | 8/2007 | |
| WO | WO-2008/005033 A1 | 1/2008 | |
| WO | WO-2008/054192 A1 | 5/2008 | |
| WO | WO-2008/071667 A1 | 6/2008 | |
| WO | WO-2008/081934 A1 | 7/2008 | |
| WO | WO-2009/051502 A1 | 4/2009 | |
| WO | WO-2009/057121 A1 | 5/2009 | |
| WO | WO-2009/066685 A1 | 5/2009 | |
| WO | WO-2009/138680 A2 | 11/2009 | |
| WO | WO-2009/154448 A1 | 12/2009 | |
| WO | WO-2010/027258 A1 | 3/2010 | |
| WO | WO-2010/027259 A1 | 3/2010 | |
| WO | WO-2010027259 A1 * | 3/2010 | ............ A61K 36/02 |
| WO | WO-2010/068086 A1 | 6/2010 | |
| WO | WO-2010/068103 A1 | 6/2010 | |
| WO | WO-2010/068105 A1 | 6/2010 | |
| WO | WO-2010/070613 A2 | 6/2010 | |
| WO | WO-2010/134810 | 11/2010 | |
| WO | WO-2011/071371 A1 | 6/2011 | |
| WO | WO-2011/108918 | 9/2011 | |
| WO | WO-2011/108934 A1 | 9/2011 | |
| WO | WO-2011/115476 | 9/2011 | |
| WO | WO-2011/115491 | 9/2011 | |
| WO | WO-2011/138457 | 11/2011 | |
| WO | WO-2012/173467 A1 | 12/2012 | |
| WO | WO-2012/173486 | 12/2012 | |
| WO | WO-2013/036102 A1 | 3/2013 | |
| WO | WO-2013/036103 A1 | 3/2013 | |
| WO | WO-2013/036104 A1 | 3/2013 | |
| WO | WO-2013/036123 A | 3/2013 | |
| WO | WO-2013/153071 A2 | 10/2013 | |
| WO | WO-2013/191533 A1 | 12/2013 | |
| WO | WO-2015/014967 A1 | 2/2015 | |
| WO | WO-2015/065193 A1 | 5/2015 | |
| WO | WO-2015/067325 | 5/2015 | |
| WO | WO-2015/078505 A1 | 6/2015 | |
| WO | WO-2015/091789 A2 | 6/2015 | |
| WO | WO-2016/024864 A1 | 2/2016 | |
| WO | WO-2017/064304 A1 | 4/2017 | |

OTHER PUBLICATIONS

Agostoni et al., "Enteral Nutrient Supply for Preterm Infants: Commentary From the European Society for Paediatric Gastroenterology, Hepatology, and Nutrition Committee on Nutrition", Journal of Pediatric Gastroenterology and Nutrition, vol. 50, No. 1, Jan. 2010, pp. 85-91 (7 pages).

Butte et al., "Energy Expenditure and Deposition of Breast-Fed and Formula-Fed Infants during Early Infancy", Pediatric Research, vol. 28, No. 6, 1990, pp. 631-640 (10 pages).

Clausen et al., "Overweight and the Metabolic Syndrome in Adult Offspring of Women with Diet-Treated Gestational Diabetes Mellitus or Type 1 Diabetes", J Clin Endocrinol Metab, vol. 94, No. 7, Jul. 2009, pp. 2464-2470 (8 pages).

Database WPI Week 198447, Thomson Scientific, London, GB, May 12, 2008, AN 1984-293720, XP-002505629 (1 page).

Eriksson et al., "Size at birth, childhood growth and obesity in adult life", International Journal of Obesity, vol. 25, 2001, pp. 735-740 (7 pages).

Gallier et al., "A novel infant milk formula concept: Mimicking the human milk fat globule structure", Colloids and Surfaces B: Biointerfaces, vol. 136, 2015, pp. 329-339 (11 pages).

International Preliminary Report on Patentability, Ch. II, for PCT/NL2014/050761 dated Mar. 9, 2016 (13 pages).

Li et al., "Do infants fed from bottles lack self regulation of milk intake compared with directly breasted infants", Pediatrics, vol. 125, pp. e1386-e1393.

Llewellyn et al., "Development and factor structure of the Baby Eating Behaviour Questionnaire in the Gemini birth cohort", Appetite, vol. 57, 2011, pp. 388-396 (9 pages).

Lubetzky et al., "Energy expenditure in human milk—versus formula-fed preterm infants", The Journal of Pediatrics, vol. 143, Issue 6, Dec. 2003, pp. 750-753 (4 pages).

Mallan et al., "Confirmatory factor analysis of the Baby Eating Behaviour Questionnaire and associations with infant weight, gender and feeding mode in an Australian sample", Appetite, vol. 82, Nov. 1, 2014, pp. 43-49 (7 pages).

Oken et al., "Gestational weight gain and child adiposity at age 3 years", American Journal of Obstetrics & Gynecology, vol. 196, Apr. 2007, pp. 322.e1-322.e8 (8 pages).

Rasmussen et al., "The relation of weight, length and ponderal index at birth to body mass index and overweight among 18-year-old males in Sweden", Abstract, European Journal of Epidemiology, vol. 14, Issue 4, Jun. 1998, pp. 373-380 (7 pages).

Snitker et al., "Effects of novel capsinoid treatment on fatness and energy metabolism in humans: possible pharmacogenetic implications", American Journal of Clinical Nutrition, vol. 89, 2009, pp. 45-50 (6 pages).

Sproston, et al., "Enzymatic Modification of Anhydrous Milkfat with n-3 and n-6 Fatty Acids for Potential Use in Infant Formula: Comparison of Methods", Journal of the American Oil Chemists' Society, vol. 93, 2016, pp. 251-265 (15 pages).

Stunkard et al., "Energy intake, not energy output, is a determinant of body size in infants", American Journal of Clinical Nutrition, vol. 69, 1999, pp. 524-530 (7 pages).

Young et al., "Biological Determinants Linking Infant Weight Gain and Child Obesity: Current Knowledge and Future Directions", Advances in Nutrition, vol. 3, 2012, pp. 675-686 (12 pages).

Fox, http://www.foxnews.com/health/2014/05/29/30-percent-world-is-now-overweight-or-obese-no-country-immune.html, accessed on Sep. 21, 2016.

Oddy, "Infant feeding and obesity risk in the child", Breastfeed Rev., Jul. 20112, vol. 20, No. 2, pp. 7-12.

Andres et al., "Body fat and bone mineral content of infants fed breast milk, cow's milk formula, or soy formula during the first year of life", The Journal of Pediatrics, 2013, vol. 163, No. 1, pp. 49-54.

Dewey et al., "Breast-fed infants are leaner than formula-fed infants at 1 y of age: the DARLING study", Am J Clin Nutr, 1993, vol. 57, pp. 140-145.

Dewey et al., "Growth of breast-fed and formula-fed infants from 0 to 18 months: The DARLING study", Pediatrics, Jun. 1992, vol. 89, No. 6, pp. 1035-1041.

Koletzko et al., "Lower protein in infant formula is associated with lower weight up to age 2 y: a randomized clinical trial", Am J Clin Nutr, 2009, vol. 89, pp. 1836-1845.

Timby et al., "Neurodevelopment, nutrition, and growth until 12 mo of age in infants fed a low-energy, low-protein formula supplemented with bovine milk fat globule membranes: a randomized controlled trial", Am J Clin Nutr. 2014, 9 pages.

"Glycosphingolipid," as accessed Oct. 5, 2015, from https://en.wikipedia.org/wiki/Glycosphingolipid.

(56) References Cited

OTHER PUBLICATIONS

Agostoni et al., "Polyunsaturated Fatty Acids in Human Milk and Neurological Development In Breastfed Infants," Current Pediatric Reviews, 1:25-30 (2005).
Benoit et al., "*Phospholipid* Species and Minor Sterols in French Human Milks in Breast Fed Infants," Food Chemistry, 120:684-691 (2010).
Database WPI Week 200937, Thompson Scientific, London, GB, AN 2009-J69887, May 28, 2009, XP002578379.
Sprong et al., "Bovine milk fat components inhibit food-borne pathogens", International Dairy Journal, 2002, vol. 12, pp. 209-215.
Durand et al., "Particle Sizes and Stability of UHT Bovine, Cereal and Grain Milks," Food Hydrocolloids, 17:671-678 (2003).
Fave et al., "Physicochemical Properties of Lipids; New Strategies to Manage Fatty Acid Bioavailability," Cellular and Molecular Biology, 50(7):815-831 (2004).
Hamilton, "Interactions of Triglycerides with Phospholipids; Incorporation into the Bilayer Structure and Formation of Emulsions," Biochemistry, 28:2514-2520 (1989).
Holman et al., "Deficiency of Essential Fatty Acids and Membrane Fluidity During Pregnancy and Lactation," Proceedings of the National Academy of Sciences of the United States Of America, 88(11):4835-4839 (1991).
Hur et al., "Influence of Initial Emulsifier Type on Microstructural Changes Occurring in Emulsified Lipids During In Vitro Digestion," Food Chemistry, 114:253-262 (2009).
InFat—The premium choice for infant formula-closer to mother's milk, Nov. 2009, AAK Magazine.
International Preliminary Report on Patentability in Application No. PCT/NL2009/050343 dated Jul. 19, 2010.
International Preliminary Report on Patentability in Application No. PCT/NL2011/050156 dated Aug. 24, 2012.
International Preliminary Report on Patentability in Application No. PCT/NL2011/050187 dated Jun. 13, 2012.
International Preliminary Report on Patentability in Application No. PCT/NL2011/050188 dated Jun. 15, 2012.
International Preliminary Report on Patentability dated Sep. 17, 2013 in International Application No. PCT/NL2012/050623.
International Search Report for PCT/NL2008/050792 dated Jul. 8, 2009.
International Search Report in Application No. PCT/NL2009/050343 dated Jul. 15, 2009.
International Search Report in Application No. PCT/NL2009/050525 dated Dec. 1, 2009 (3 pages).
International Search Report in Application No. PCT/NL2009/050526 dated Dec. 14, 2009.
International Search Report in Application No. PCT/NL2009/050754 dated May 7, 2010.
International Search Report in Application No. PCT/NL2009/050756 dated May 11, 2010.
International Search Report in Application No. PCT/NL2011/050156 dated Jun. 1, 2011.
International Search Report in Application No. PCT/NL2011/050187 dated Jul. 5, 2011.
International Search Report in Application No. PCT/NL2011/050188 dated Jul. 5, 2011.
International Search Report in PCT/NL2010/050108 dated Nov. 11, 2010.
International Search Report in PCT/NL2010/050142 dated Mar. 2, 2011.
International Search Report dated Oct. 30, 2012 in International Application No. PCT/NL2012/050623.
Jensen et al., "Specialty Lipids for Infant Nutrition. I. Milks and Formulas," Journal of Pediatric Gastroenterlogy and Nutrition, 15(3):232-245 (1992).
Joscelyne et al., "Food Emulsions Using Membrane Emulsification; Conditions for Producing Small Droplets," Journal of Food Engineering, 39:59-64(1999).
Lucas Alan, "Long-Term Programming Effects of Early Nutrition—Implications for the Preterm Infant", Journal of Perinatology (2005) 25, S2-S6.
Makrides et al., "Fatty Acid Composition of Brain, Retina, and Erythrocytes in Breast- and Formula-Fed Infants," American Journal of Clinical Nutrition (US), 60(2):189-194 (1994).
Marmot, et al. "Effect of breast-feeding on plasma cholesterol and weight in young adults", Journal of Epidemiology and Community Health (1980), vol. 34, pp. 164-167.
McClements, "Food Emulsions—Principles, Practices, and Techniques," CRC Press, Inc., Second Edition, Section 7.3 (2005).
Michalski et al., "Optical Parameters of Milk Fat Globules for Laser Light Scattering Measurements," Lait, 81(6):787-796 (2001).
Michalski et al., "Size Distribution of Fat Globules in Human Colostrum, Breast Milk, and Infant Formula," Journal of Dairy Science, American Dairy Science Association, 88:1927-1940 (2005).
Michalski et al., "The Dispersion State of Milk Fat Influences Triglyceride Metabolism in the Rat," European Journal of Nutrition, 44:436-444 (2005).
Michalski, "The Supramolecular Structure of Milk Fat Influences Plasma Triacylglycerols and Fatty Acid Profile in the Rat," European Journal of Nutrition, 45:215-224 (2006).
Mun et al., "Influence of Interfacial Composition on In Vitro Digestibility of Emulsified Lipids: Potential Mechanism for Chitosan's Ability to Inhibit Fat Digestion," Food Biophysics, 1:21-29 (2006).
Osteoporosis, PubMed Health, available at http;www.ncbi.nlm.nih.gov/pubmedhealth/PMH0001400, 2012.
Owen, et al. "Infant Feeding and Blood Cholesterol: A Study in Adolescents and a Systematic Review", Pediatrics (2006) vol. 110, pp. 597-608.
Park et al., "Influence of Encapsulation of Emulsified Lipids With Chitosan on Their In Vivo Digestibility," Food Chemistry, 104:761-767 (2007).
Petrowski, "Emulson Stability and Its Relation to Foods," Emulsion Stability, 309-359 (1976).
Ruegg et al., "The Fat Globule Size Distribution in Human Milk," Biochimica et Biophysica Acta, 666:7-14 (1981).
Schultz et al., "High-Pressure Homogenization as a Process for Emulsion Formation," Chemical Engineering Technology, 27(4):361-368 (2004).
Simonin et al., "Comparison of the Fat Content and Fat Globule Size Distribution of Breast Milk From Mothers Delivering Term and Preterm," The American Journal of Clinical Nutrition, 40:820-826 (1984).
Vickers, et al., "Supplementation with a Mixture of Complex Lipids Derived from Milk to Growing Rats Results in Improvements in Parameters Related to Growth and Cognition," Nutrition Research, 29:426-435 (2009).
Whittlestone et al., "Variations in the Fat Content of Human Milk During Suckling," Ruakura Animal Research Station, Department of Agriculture, 204-206 (1953).
International Search Report issued International Patent Application No. PCT/NL2014/050761, dated Jan. 26, 2015.
U.S. Appl. No. 14/343,814, US 2014-0248391, Daniel E. Coughlin.
U.S. Appl. No. 14/966,889, US 2016-0199331, Rachel Eva Bredefeld.
U.S. Appl. No. 14/658,054, US 2015-0306117, Nicole Plourde Babson.
U.S. Appl. No. 13/635,389, US 2013-0071446, Sarah J. Chickos.
U.S. Appl. No. 13/582,325, US 2013-0052297, Philip A. Dubois.
U.S. Appl. No. 13/914,405, US 2014-0093554, Daniel E. Coughlin.
U.S. Appl. No. 15/091,080, US 2016-0219915, Sean M. Basquill.
U.S. Appl. No. 15/079,853, US 2016-0205983, Sean M. Basquill.
U.S. Appl. No. 14/408,940, US 2015-0173405, Daniel E. Coughlin.
U.S. Appl. No. 13/061,643, US 2011-0206743, Basquill, Sean M.
U.S. Appl. No. 13/061,698, US 2011-0217411, Basquill, Sean M.
U.S. Appl. No. 13/133,929, US 2011-00300204, Daniel E. Coughlin.
U.S. Appl. No. 13/133,924, US 2011-0300225, Snigdha Maewall.
U.S. Appl. No. 15/259,537, US 2017-0151203, Sarah J. Chickos.
U.S. Appl. No. 13/635,381, US 2013-0096087, Nicole Plourde Babson.
U.S. Appl. No. 14/343,814, US 2014-0248391, Daniel F. Coughlin.
U.S. Appl. No. 14/435,131, US 2015-0265540, Rachel Eva Bredefeld.
U.S. Appl. No. 15/259,881, US 2017-0151175, Rachel Eva Bredefeld.

(56) References Cited

OTHER PUBLICATIONS

U.S. Appl. No. 15/033,471, US 2016-0263033, Rachel Eva Bredefeld.
U.S. Appl. No. 15/503,930, US 2017-0273343, Danah Al-Awadi.
U.S. Appl. No. 15/768,195, US 2018-0296481, Hasan S. Ahmed.
U.S. Appl. No. 15/768,202, US 2018-0310605, Daniel F. Coughlin.
U.S. Appl. No. 16/435,141, US 2019-0289893, Erik Kashnikow.
U.S. Appl. No. 16/586,403, US 2020-0022396, Unassigned.

* cited by examiner

LIPID COMPOSITION FOR IMPROVING BODY COMPOSITION DURING CATCH-UP GROWTH

CROSS-REFERENCE TO RELATED APPLICATIONS

This application is a divisional application of U.S. patent application Ser. No. 15/033,471 filed Apr. 29, 2016 which application is the National Phase of International Patent Application No. PCT/NL2014/050761, filed Nov. 3, 2014, published on May 7, 2015 as WO 2015/065193 A1, which claims priority to European Patent Application No. 13191300.6, filed Nov. 1, 2013. The contents of which are herein incorporated by reference in their entirety.

FIELD OF THE INVENTION

The invention relates to nutritional compositions for preterm or low birth weight infants

BACKGROUND OF THE INVENTION

Human milk is generally recognized as the ideal feeding for infants due to its overall nutritional composition. For a preterm infant and/or infant small for gestational age (SGA infant), however, the milk of their own mother does not always meet their complete nutritional needs, even though the milk of mothers of preterm infants appears to be adapted to the specific needs of preterms. Therefore, for these infants special nutritional formulae have been designed and marketed, which differ in composition from standard infant formula. Typically such preterm formulae have a higher energy and protein content, to enable an increased growth rate. A review on the ESPGHAN nutritional guidelines for such formulae is given in Agostoni et al, JPGN 2010, 50:85-91.

After birth, initially these preterm and/or SGA infants grow more rapidly than term infants. The growth patterns of SGA infants compensate for the growth retardation which they have developed in utero and this compensation by a sudden spurt of growth is known as "catch-up growth". It is desirable to ensure that reduced growth is compensated, but is also important that catch-up growth should not be excessive as there are indications that periods of very rapid and/or very extensive catch-up growth, particularly during infancy, may be linked with a risk of future obesity and/or diabetes type 2. It is also important that during catch-up growth no excessive adipose tissue, in particular visceral adipose tissue, is formed.

WO 2005/063050 relates to a method of increasing lean body mass and reducing fat body mass in infants, said method comprising administration to an infant a nutritional formula comprising a source of docosahexaenoic acid (DHA) and arachidonic acid (ARA) without impacting the total overall growth of the infant. This method is disclosed to be especially useful in preterm infants. WO 98/44917 relates to a method for enhancing the growth of preterm infants involving the administration of certain long chain polyunsaturated fatty acids (LC-PUFA). It is preferred that the infants are administered an infant formula containing a combination of DHA and ARA. WO 2007/039596 relates to a nutritional formulation comprising an n3 LC-PUFA, a prebiotic fibre and a probiotic bacterial strain to promote catch-up growth in young mammals whose growth has been retarded because the young mammal has been subjected to physical or mental stress. WO 2010/134810 discloses a human milk fortifier with DHA for use in preventing visceral adiposity. WO 2010/027259 discloses a nutritional composition for infants and/or toddlers comprising a lipid component which has a large lipid globule size. The composition can be used to prevent obesity and/or improve body composition later in life. A similar good growth and development early in life, with no effect on adipose tissue mass early in life was observed, which was found to be advantageous for infants and young children in general. WO 2012/173486 relates to the use of specifically designed lipid for an early in life diet for improving the development of a healthy body composition, in particular prevention of obesity, later in life.

SUMMARY OF THE INVENTION

Using a model with intrauterine growth restricted (IUGR) animals, which is representative for infants undergoing catch up growth, in particular for SGA infants and/or for preterm infants, the inventors found that a nutritional composition comprising large lipid globules and/or lipid globules coated with phospholipids (PL-coated globules) promoted controlled catch-up growth after birth. Animals having experienced catch-up growth on a standard, control diet with small lipid globules and no phospholipid coating developed an increased absolute amount and an increased relative amount of adipose tissue, in particular visceral adipose tissue, during catch-up growth. Surprisingly, in animals having experienced catch-up growth on the present experimental diet with large lipid globules and/or PL-coated lipid globules, an improved body composition was observed compared to animals receiving a control formula. The improved body composition observed was revealed as a decreased absolute amount and a decreased relative amount of adipose tissue (based on body weight), and most importantly especially a decreased relative amount of visceral adipose tissue (based on body weight or total adipose tissue mass), while on the other hand the relative amount of subcutaneous adipose tissue was increased. In the context of the present invention this is called 'promoting controlled catch-up growth'. Even more surprisingly, the decreased relative amount of visceral adipose tissue mass concomitant with increased relative amount of subcutaneous adipose tissue mass observed during catch-up growth with the experimental diet was highest in the IUGR rats, and higher than compared to control rats or sham operated rats having consumed the experimental diet. This shows that the experimental diet is especially beneficial and more effective in this specific group.

Preterm and/or SGA infants, as well as other infants experiencing catch-up growth (e.g. convalescing infants), already have an extra risk for development of visceral obesity, insulin resistance and/or metabolic disease. However, the presence of subcutaneous adipose tissue is of crucial importance for a healthy development of growth in infants, especially in preterm and/or SGA infants. Subcutaneous fat is not associated with health problems, and is furthermore necessary for a good start in life in providing energy reserves, and thermal and mechanical protection in this vulnerable group. Therefore a mere reduction in overall adipose tissue mass and/or an increase in lean body mass alone is not a way to solve the problems of increased risk of developing obesity and associated disorders in infants, and especially not in preterm and/or SGA infants. The reduced amount of visceral adipose tissue, while having an increase in subcutaneous adipose tissue, as specifically observed during catch-up growth in the IUGTR group, is therefore very advantageous for infants undergoing catch up growth, such as preterm infants, SGA infants, and/or infants with retarded growth due to physical or mental stress after birth (e.g. convalescing infants).

DETAILED DESCRIPTION OF THE INVENTION

Thus the present invention concerns a method for promoting controlled catch-up growth in an infant selected from the group consisting of preterm infants, small for gestational age infants and infants with retarded growth due to physical or mental stress after birth, comprising administering to said infant a nutritional composition comprising lipid, wherein the lipid is present in lipid globules having:
- (a) a volume-weighted mode diameter of at least 1.0 µm; and/or
- (b) a phospholipid coating, wherein the nutritional composition comprises at least 0.5 wt. % phospholipids based on total lipid.

Thus, the invention concerns a method for promoting controlled catch-up growth in an infant selected from the group consisting of preterm infants, small for gestational age infants and infants with retarded growth due to physical or mental stress after birth, comprising administering to said infant a nutritional composition comprising lipid, wherein the lipid is present in lipid globules, having a volume-weighted mode diameter of at least 1.0 µm.

The invention also concerns a method for promoting controlled catch-up growth in an infant selected from the group consisting of preterm infants, small for gestational age infants and infants with retarded growth due to physical or mental stress after birth, comprising administering to said infant a nutritional composition comprising lipid, wherein the lipid is present in lipid globules, having a phospholipid coating, wherein the nutritional composition comprises at least 0.5 wt. % phospholipids based on total lipid.

The invention also concerns a method for promoting controlled catch-up growth in an infant selected from the group consisting of preterm infants, small for gestational age infants and infants with retarded growth due to physical or mental stress after birth, comprising administering to said infant a nutritional composition comprising protein, carbohydrates and lipid, wherein the lipid is present in lipid globules, having a volume-weighted mode diameter of at least 1.0 µm, and having a phospholipid coating, wherein the nutritional composition comprises at least 0.5 wt. % phospholipids based on total lipid.

In other words, the present invention concerns the use of lipid for the preparation of a nutritional composition for promoting controlled catch-up growth in an infant selected from the group consisting of preterm infants, small for gestational age infants and infants with retarded growth due to physical or mental stress after birth, wherein the lipid is present in lipid globules, having:
- (a) a volume-weighted mode diameter of at least 1.0 µm; and/or
- (b) a phospholipid coating, wherein the nutritional composition comprises at least 0.5 wt. % phospholipids based on total lipid.

Thus, the invention concerns the use of lipid for the preparation of a nutritional compositions for promoting controlled catch-up growth in an infant selected from the group consisting of preterm infants, small for gestational age infants and infants with retarded growth due to physical or mental stress after birth, wherein the lipid is present in lipid globules, having a volume-weighted mode diameter of at least 1.0 µm.

The invention also concerns the use of lipid for the preparation of a nutritional compositions for promoting controlled catch-up growth in an infant selected from the group consisting of preterm infants, small for gestational age infants and infants with retarded growth due to physical or mental stress after birth, wherein the lipid is present in lipid globules, having a phospholipid coating, wherein the nutritional composition comprises at least 0.5 wt. % phospholipids based on total lipid.

The invention also concerns the use of lipid for the preparation of a nutritional compositions for promoting controlled catch-up growth in an infant selected from the group consisting of preterm infants, small for gestational age infants and infants with retarded growth due to physical or mental stress after birth, wherein the lipid is present in lipid globules, having a volume-weighted mode diameter of at least 1.0 and having a phospholipid coating, wherein the nutritional composition comprises at least 0.5 wt. % phospholipids based on total lipid.

The present invention can also be worded as a nutritional composition comprising lipid, wherein the lipid is present in lipid globules, having:
- (a) a volume-weighted mode diameter of at least 1.0 µm; and/or
- (b) a phospholipid coating, wherein the nutritional composition comprises at least 0.5 wt. % phospholipids based on total lipid, for use in promoting controlled catch-up growth in an infant selected from the group consisting of preterm infants, small for gestational age infants and infants with retarded growth due to physical or mental stress after birth.

Thus, the invention concerns a nutritional compositions comprising lipid, wherein the lipid is present in lipid globules, having a volume-weighted mode diameter of at least 1.0 for use in promoting controlled catch-up growth in an infant selected from the group consisting of preterm infants, small for gestational age infants and infants with retarded growth due to physical or mental stress after birth.

The invention also concerns a nutritional composition comprising lipid, wherein the lipid is present in lipid globules, having a phospholipid coating, wherein the nutritional composition comprises at least 0.5 wt. % phospholipids based on total lipid, for use in promoting controlled catch-up growth in an infant selected from the group consisting of preterm infants, small for gestational age infants and infants with retarded growth due to physical or mental stress after birth.

The invention also concerns a nutritional composition comprising lipid, wherein the lipid is present in lipid globules, having a volume-weighted mode diameter of at least 1.0 µm, and having a phospholipid coating, wherein the nutritional composition comprises at least 0.5 wt. % phospholipids based on total lipid, for use in promoting controlled catch-up growth in an infant selected from the group consisting of preterm infants, small for gestational age infants and infants with retarded growth due to physical or mental stress after birth.

Thus the present invention concerns a method for (i) improving body composition, (ii) improving adipose tissue distribution, (iii) decreasing visceral adipose tissue based on body weight and/or on total adipose tissue, and/or (iv) decreasing the ratio visceral adipose tissue to subcutaneous adipose tissue, in an infant selected from the group consisting of preterm infants, small for gestational age infants and infants with retarded growth due to physical or mental stress after birth, comprising administering to said infant a nutritional composition comprising lipid, wherein the lipid is present in lipid globules having:
- (a) a volume-weighted mode diameter of at least 1.0 µm; and/or
- (b) a phospholipid coating, wherein the nutritional composition comprises at least 0.5 wt. % phospholipids based on total lipid.

Thus, the invention concerns a method for (i) improving body composition, (ii) improving adipose tissue distribution, (iii) decreasing visceral adipose tissue based on body weight and/or on total adipose tissue, and/or (iv) decreasing the ratio visceral adipose tissue to subcutaneous adipose tissue, in an infant selected from the group consisting of preterm infants, small for gestational age infants and infants with retarded growth due to physical or mental stress after birth, comprising administering to said infant a nutritional composition comprising lipid, wherein the lipid is present in lipid globules, having a volume-weighted mode diameter of at least 1.0 µm.

The invention also concerns a method for (i) improving body composition, (ii) improving adipose tissue distribution, (iii) decreasing visceral adipose tissue based on body weight and/or on total adipose tissue, and/or (iv) decreasing the ratio visceral adipose tissue to subcutaneous adipose tissue, in an infant selected from the group consisting of preterm infants, small for gestational age infants and infants with retarded growth due to physical or mental stress after birth, comprising administering to said infant a nutritional composition comprising lipid, wherein the lipid is present in lipid globules, having a phospholipid coating, wherein the nutritional composition comprises at least 0.5 wt. % phospholipids based on total lipid.

The invention also concerns a method for (i) improving body composition, (ii) improving adipose tissue distribution, (iii) decreasing visceral adipose tissue based on body weight and/or on total adipose tissue, and/or (iv) decreasing the ratio visceral adipose tissue to subcutaneous adipose tissue, growth in an infant selected from the group consisting of preterm infants, small for gestational age infants and infants with retarded growth due to physical or mental stress after birth, comprising administering to said infant a nutritional composition comprising protein, carbohydrates and lipid, wherein the lipid is present in lipid globules, having a volume-weighted mode diameter of at least 1.0 µm, and having a phospholipid coating, wherein the nutritional composition comprises at least 0.5 wt. % phospholipids based on total lipid.

In one embodiment, the method for (i) improving body composition, (ii) improving adipose tissue distribution, (iii) decreasing visceral adipose tissue based on body weight and/or on total adipose tissue, and/or (iv) decreasing the ratio visceral adipose tissue to subcutaneous adipose tissue, in an infant selected from the group of preterm infants, small for gestational age infants and infants with retarded growth due to physical or mental stress after birth, is a non-therapeutic method or a non-medical method.

In other words, the present invention concerns the use of lipid for the preparation of a nutritional composition for (i) improving body composition, (ii) improving adipose tissue distribution, (iii) decreasing visceral adipose tissue based on body weight and/or on total adipose tissue, and/or (iv) decreasing the ratio visceral adipose tissue to subcutaneous adipose tissue, in an infant selected from the group consisting of preterm infants, small for gestational age infants and infants with retarded growth due to physical or mental stress after birth, wherein the lipid is present in lipid globules, having:
- (a) a volume-weighted mode diameter of at least 1.0 µm; and/or
- (b) a phospholipid coating, wherein the nutritional composition comprises at least 0.5 wt. % phospholipids based on total lipid.

Thus, the invention concerns the use of lipid for the preparation of a nutritional compositions for (i) improving body composition, (ii) improving adipose tissue distribution, (iii) decreasing visceral adipose tissue based on body weight and/or on total adipose tissue, and/or (iv) decreasing the ratio visceral adipose tissue to subcutaneous adipose tissue, in an infant selected from the group consisting of preterm infants, small for gestational age infants and infants with retarded growth due to physical or mental stress after birth, wherein the lipid is present in lipid globules, having a volume-weighted mode diameter of at least 1.0 µm.

The invention also concerns the use of lipid for the preparation of a nutritional compositions for (i) improving body composition, (ii) improving adipose tissue distribution, (iii) decreasing visceral adipose tissue based on body weight and/or on total adipose tissue, and/or (iv) decreasing the ratio visceral adipose tissue to subcutaneous adipose tissue, in an infant selected from the group consisting of preterm infants, small for gestational age infants and infants with retarded growth due to physical or mental stress after birth, wherein the lipid is present in lipid globules, having a phospholipid coating, wherein the nutritional composition comprises at least 0.5 wt. % phospholipids based on total lipid.

The invention also concerns the use of lipid for the preparation of a nutritional compositions for (i) improving body composition, (ii) improving adipose tissue distribution, (iii) decreasing visceral adipose tissue based on body weight and/or on total adipose tissue, and/or (iv) decreasing the ratio visceral adipose tissue to subcutaneous adipose tissue, in an infant selected from the group consisting of preterm infants, small for gestational age infants and infants with retarded growth due to physical or mental stress after birth, wherein the lipid is present in lipid globules, having a volume-weighted mode diameter of at least 1.0 µm, and having a phospholipid coating, wherein the nutritional composition comprises at least 0.5 wt. % phospholipids based on total lipid.

The present invention can also be worded as a nutritional composition comprising lipid, wherein the lipid is present in lipid globules, having:
- (a) a volume-weighted mode diameter of at least 1.0 µm; and/or
- (b) a phospholipid coating, wherein the nutritional composition comprises at least 0.5 wt. % phospholipids based on total lipid, for use in (i) improving body composition, (ii) improving adipose tissue distribution, (iii) decreasing visceral adipose tissue based on body weight and/or on total adipose tissue, and/or (iv) decreasing the ratio visceral adipose tissue to subcutaneous adipose tissue, in an infant selected from the group consisting of preterm infants, small for gestational age infants and infants with retarded growth due to physical or mental stress after birth.

Thus, the invention concerns a nutritional compositions comprising lipid, wherein the lipid is present in lipid globules, having a volume-weighted mode diameter of at least 1.0 µm, for use in (i) improving body composition, (ii) improving adipose tissue distribution, (iii) decreasing visceral adipose tissue based on body weight and/or on total adipose tissue, and/or (iv) decreasing the ratio visceral adipose tissue to subcutaneous adipose tissue, in an infant selected from the group consisting of preterm infants, small for gestational age infants and infants with retarded growth due to physical or mental stress after birth.

The invention also concerns a nutritional composition comprising lipid, wherein the lipid is present in lipid globules, having a phospholipid coating, wherein the nutritional composition comprises at least 0.5 wt. % phospholipids based on total lipid, for use in (i) improving body composition, (ii) improving adipose tissue distribution, (iii) decreasing visceral adipose tissue based on body weight and/or on total adipose tissue, and/or (iv) decreasing the ratio visceral adipose tissue to subcutaneous adipose tissue, in an infant selected from the group consisting of preterm infants, small for gestational age infants and infants with retarded growth due to physical or mental stress after birth.

The invention also concerns a nutritional composition comprising lipid, wherein the lipid is present in lipid globules, having a volume-weighted mode diameter of at least 1.0 µm, and having a phospholipid coating, wherein the nutritional composition comprises at least 0.5 wt. % phospholipids based on total lipid, for use in (i) improving body composition, (ii) improving adipose tissue distribution, (iii) decreasing visceral adipose tissue based on body weight and/or on total adipose tissue, and/or (iv) decreasing the ratio visceral adipose tissue to subcutaneous adipose tissue, in an infant selected from the group consisting of preterm infants, small for gestational age infants and infants with retarded growth due to physical or mental stress after birth.

Preferably, the nutritional composition is an infant formula, more preferably a preterm formula, low birthweight formula or paediatric formula for catch-up growth, which is intended for providing nutrition to an infant selected from the group consisting of preterm infants, small for gestational age infants and infants with retarded growth due to physical or mental stress after birth.

In another aspect, the invention concerns an infant formula, more preferably a preterm formula, low birthweight formula or paediatric formula for catch-up growth, which is intended for providing nutrition to an infant selected from the group consisting of preterm infants, small for gestational age infants and infants with retarded growth due to physical or mental stress after birth. Herein, a "preterm formula" is to be understood as an infant formula intended for and/or especially designed for preterm infants. Herein, a "low birthweight formula" is to be understood as an infant formula intended for and/or especially designed for small for gestational age infants. Herein, a "paediatric formula for catch-up growth" is to be understood as an infant formula intended for and/or especially designed for infants with retarded growth due to physical or mental stress after birth such as convalescent infants.

In another aspect, the invention concerns the use of the nutritional composition according to the invention for providing nutrition to an infant selected from the group consisting of preterm infants, small for gestational age infants and infants with retarded growth due to physical or mental stress after birth.

This aspect could also be worded as the use of lipid for the preparation of the nutritional composition according to the invention for providing nutrition to an infant selected from the group consisting of preterm infants, small for gestational age infants and infants with retarded growth due to physical or mental stress after birth.

This aspect could also be worded as a method for providing nutrition to an infant selected from the group consisting of preterm infants, small for gestational age infants and infants with retarded growth due to physical or mental stress after birth, comprising administering the nutritional composition according to the invention to said infant.

This aspect could also be worded as the nutritional composition according to the invention for use in providing nutrition to an infant selected from the group consisting of preterm infants, small for gestational age infants and infants with retarded growth due to physical or mental stress after birth.

Target Group

The present invention relates to a method for feeding preterm infants, small for gestational age (SGA) infants, and/or infants with retarded growth due to physical or mental stress after birth, preferably for feeding premature infants, small for gestational age (SGA) infants and/or convalescent infants, more preferably for feeding preterm infants and/or small for gestational age (SGA) infants. A preterm infant relates to an infant born before the standard period of pregnancy is completed, thus before 37 weeks pregnancy of the mother, i.e. before 37 weeks from the beginning of the last menstrual period of the mother. Preterm infants are also referred to as premature infants.

SGA infants are those whose birth weight lies below the 10th percentile for that gestational age. Reasons for SGA can be several; for example, term or preterm infants can be born SGA because they have been the subject of intrauterine growth restriction (IUGR). Many preterm infants are also small for gestational age. Premature and/or SGA infants include low birth weight infants (LBW infants), very low birth weight infants (VLBW infants), and extremely low birth weight infants (ELBW infants). LBW infants are infants with a birth weight below 2500 g; this group includes term infants born SGA. VLBW and ELBW infants are almost always born preterm and are defined as infants with a birth weight below 1500 g or 1000 g, respectively.

Infants with retarded growth due to physical or mental stress after birth are infants that need to recover from a disease state after birth in the first year of life, thus from 0-12 months. Such recovering infants can also be referred to as convalescent infants.

Catch-up growth, also referred to as compensatory growth, is known in the art to be distinct from regular growth and is defined as the accelerated growth of subjects following a period of reduced or incomplete growth or growth retardation. A practical definition of catch-up growth is an increase in weight above 0.67 Standard Deviation (SD) score, as for example can be visualised in standard growth charts, suitably spanning the first 24 months of life of an infant, by crossing a centile band. Reduced growth may occur due to nutrient deprivation, e.g. poor maternal nutrition during pregnancy or lack of adequate oxygen supply to the fetus, leading to intrauterine growth restriction, or poor nutrition during sickness or chronic illness. Also preterm infants, which have not experienced intrauterine growth restriction but are delivered before the standard period of pregnancy is completed, generally with a lower than average birth weight, usually exhibit catch-up growth. Growth retardation can also occur due to physical or mental stress, for example due to a disease, in infants in the first year of life. Such infants experiencing growth retardation can have been appropriate for gestational age (AGA) at birth. The body weights of subjects who experienced reduced or incomplete growth or growth retardation will over time become similar to those of subjects who did not experience such stress. Such a high compensatory growth rate may result in overcompensation, where the normal weight is exceeded and the animal in suit often develops excessive adipose tissue deposition during catch-up growth. Herein, "subject" preferably refers to human, and "infant" preferably refers to "human infant". Human infants are defined as human subjects between 0 and 12 months of age.

The nutritional composition according to the present invention is thus especially beneficial for preterm infants, small for gestational age infants and infants with retarded growth due to physical or mental stress after birth, as those are likely to have experienced reduced or incomplete growth and likely are experiencing or will experience catch-up growth. Thus, the target group for the present invention is selected from preterm infants, small for gestational age infants (SGA infants, including IUGR infants) and infants with retarded growth due to physical or mental stress after birth, preferably human infants. Preferably, the target group is selected from preterm infants and SGA infants, more preferably SGA infants. A preferred group of SGA infants are the IUGR (intrauterine growth restricted) infants.

Preferably, the nutritional composition is an infant formula, more preferably a preterm formula or low birthweight formula or paediatric formula for catch-up growth, which is intended for providing nutrition to an infant selected from the group consisting of preterm infants, small for gestational age infants and infants with retarded growth due to physical or mental stress after birth.

Body Adipose Tissue Distribution, Visceral Adiposity

The term 'visceral adiposity' refers to a condition wherein the subject has increased visceral tissue mass. The term visceral adiposity is also referred to as visceral obesity, intra-abdominal obesity or central obesity. Visceral adiposity is typically caused by (accumulation of) excessive visceral tissue mass. Visceral tissue, also known as visceral fat, organ fat, intra-abdominal fat, peritoneal fat or central fat is normally located inside the peritoneal cavity as opposed to subcutaneous fat which is found underneath the skin and intramuscular fat which is found interspersed in skeletal muscles. Visceral fat includes mesenteric fat, perineal fat and retroperitoneal fat. Visceral fat stores can suitably be investigated by imaging techniques such as computed tomography (CT), magnetic resonance imaging (MM) and ultrasonography. Total adipose tissue mass can be determined by DEXA (dual-energy X-ray absorptiometry). Internal abdominal adipose tissue is a synonym for intra-abdominal adipose tissue or visceral adipose tissue, and is the adipose tissue that surrounds the internal organs.

In the present invention, improving body composition or improving adipose tissue distribution may encompass a decrease in visceral adipose tissue mass, based on body weight and/or based on total adipose tissue, an increase in subcutaneous adipose tissue mass, based on total adipose tissue, and/or a decrease in the weight ratio of visceral adipose tissue to subcutaneous adipose tissue. Thus, a reduction of total adipose tissue mass is not aimed for.

In one particular embodiment, the present invention is also for the prevention of, in particular prevention of accumulation of, excessive visceral adipose tissue mass or for the prevention of visceral adiposity. Herein, the term "prevention" can also be referred to as "reducing the risk or occurrence of" for example visceral adiposity. Herein, each of "preventing visceral adiposity" "improving body composition", "improving adipose tissue distribution", "decreasing visceral adipose tissue mass", "increasing subcutaneous adipose tissue mass", and "decreasing the weight ratio of visceral adipose tissue to subcutaneous adipose tissue", is compared to the situation regarding preterm infants, SGA infants and infants with retarded growth due to physical or mental stress after birth which are not administered with a nutritional composition according to the present invention, i.e. administered with a conventional nutritional composition. Thus, the occurrence of visceral adiposity, the body composition, the adipose tissue distribution, the visceral adipose tissue mass, the subcutaneous adipose tissue mass and/or the weight ratio of visceral adipose tissue to subcutaneous adipose tissue is more like the situation regarding healthy breast-fed term born infants with the same gestational age having a weight and size appropriate for gestational age.

Lipid

The present nutritional composition comprises lipid in the form of lipid globules. Preferably more than 95 wt. % of the lipid present in the nutritional composition is in the form of lipid globules, preferably more than 98 wt. % of the lipid present in the nutritional composition is in the form of lipid globules. The lipid that is present in the nutritional composition provides preferably 30 to 60% of the total calories of the composition. More preferably the present nutritional composition comprises lipid providing 35 to 55% of the total calories, even more preferably the present composition comprises lipid providing 40 to 50% of the total calories. Per 100 kcal, the nutritional composition preferably comprises 4.4 to 6.0 g lipid, more preferably 4.6 to 5.5 g lipid. When in liquid form, e.g. as a ready-to-feed liquid, the nutritional composition preferably comprises 2.1 to 6.5 g lipid per 100 ml, more preferably 3.0 to 6.0 g per 100 ml. In case the present nutritional composition is a preterm formula or low birthweight formula, it is preferred that the composition comprises 3.0 to 5.0 g lipid per 100 ml, more preferably 3.5 to 4.5 g per 100 ml. In case the present nutritional composition is a paediatric formula for catch-up growth, it is preferred that the composition comprises 4.0 to 6.0 g lipid per 100 ml, more preferably 4.5 to 5.5 g per 100 ml. Based on dry weight the nutritional composition preferably comprises 10 to 50 wt. %, more preferably 12.5 to 40 wt. % lipid, even more preferably 19 to 32 wt. % lipid.

Lipids include polar lipids (such as phospholipids, glycolipids, sphingomyelin, and cholesterol), monoglycerides, diglycerides, triglycerides and free fatty acids. Preferably the nutritional composition comprises at least 75 wt. %, more preferably at least 85 wt. % triglycerides based on total lipids.

The lipid that is present in nutritional composition according to the invention preferably comprises vegetable lipids. The presence of vegetable lipids advantageously enables an optimal fatty acid profile, high in (poly)unsaturated fatty acids and/or more reminiscent to human milk fat. Using lipids from cow's milk alone, or other domestic mammals, does not provide an optimal fatty acid profile. This less optimal fatty acid profile, such as a large amount of saturated fatty acids, is known to result in increased risk of developing obesity. Preferably the present composition comprises at least one, preferably at least two lipid sources selected from the group consisting of linseed oil (flaxseed oil), rape seed oil (such as colza oil, low erucic acid rape seed oil and canola oil), salvia oil, perilla oil, purslane oil, lingonberry oil, sea buckthorn oil, hemp oil, sunflower oil, high oleic sunflower oil, safflower oil, high oleic safflower oil, olive oil, black currant seed oil, echium oil, coconut oil, palm oil and palm kernel oil. Preferably the present composition comprises at least one, preferably at least two lipid sources selected from the group consisting of linseed oil, canola oil, coconut oil, sunflower oil and high oleic sunflower oil. Commercially available vegetable lipids are typically offered in the form of a continuous oil phase. When in liquid form, e.g. as a ready-to-feed liquid, the composition preferably comprises 2.1 to 6.5 g vegetable lipid per 100 ml, more preferably 3.0 to 4.0 g per 100 ml. Based on dry weight the present composition preferably comprises 10 to 50 wt. %, more preferably 12.5 to 40 wt. % vegetable lipid, even more preferably 19 to 30 wt. %. Preferably the composition comprises 50 to 100 wt. % vegetable lipids based on total lipids, more preferably 70 to 100 wt. %, even more preferably 75 to 97 wt. %. It is noted therefore that the present composition also may comprise non-vegetable lipids. Suitable and preferred non-vegetable lipids are further specified below.

Lipid Globule Size

According to the present invention, lipid is present in the composition in the form of lipid globules, emulsified in the aqueous phase. The lipid globules according to a preferred embodiment of the present invention have a volume-weighted mode diameter of at least 1.0 μm, preferably at least 3.0 μm, more preferably at least 4.0 μm, preferably a volume-weighted mode diameter of 1.0 to 10 μm, more preferably 2.0 to 8.0 μm, even more preferably 3.0 to 8.0 μm, most preferably 4.0 to 8.0 μm. More preferably, the lipid globules also have a size distribution in such a way that at least 45 vol. %, preferably at least 55 vol. %, even more preferably at least 65 vol. %, even more preferably at least 75 vol. % of the lipid globules has a diameter of 2 to 12 μm. More preferably at least 45 vol. %, preferably at least 55 vol. %, even more preferably at least 65 vol. %, even more preferably at least 75 vol. % of the lipid globules has a volume-weighted mode diameter of 2 to 10 μm. Even more preferably at least 45 vol. %, preferably at least 55 vol. %, even more preferably at least 65 vol. %, even more preferably at least 75 vol. % of the lipid globules has a volume-weighted mode diameter of 4 to 10 μm.

The volume percentage (volume % or vol. %) of lipid globules is based on the volume of total lipid in the nutritional composition. The volume-weighted mode diameter relates to the lipid globule diameter which is the most present, based on the contribution to the volume of total lipid, or—in other words—the peak value in a graphic representation, having on the X-as the diameter and on the Y-as the volume %. The volume of the lipid globule and its size distribution can suitably be determined using a particle size analyzer such as a Mastersizer (Malvern Instruments, Malvern, UK), for example by the method described in Michalski et al, 2001, Lait 81: 787-796.

Polar Lipids

The present nutritional composition preferably comprises phospholipids (PL) and more preferably PL and other polar lipids. Polar lipids are amphipathic of nature and include glycerophospholipids, glycosphingolipids, sphingomyelin and/or cholesterol. Phospholipids are the sum of glycerophospholipids and sphingomyelin. Polar lipids in the present invention relate to the sum of glycerophospholipids, glycosphingolipids, sphingomyelin and cholesterol. Preferably the polar lipids are present as a coating or outer layer of the lipid globules. The presence of polar lipids as a coating or outer layer of the lipid globules was found to advantageously further decrease adipose tissue, in particular visceral adipose tissue. The presence of polar lipids helps to maintain the lipid globules emulsified in the aqueous composition. This is especially important when the lipid globule size is large.

Thus, in one embodiment according to the present invention the lipid globules are coated with a layer of polar lipids, preferably at least with phospholipids, wherein the nutritional composition comprises at least 0.5 wt % phospholipids based on total lipid. Such globules may be referred to as "PL-coated globules". Thus preferably the lipid globules comprise a core and a coating. In this embodiment, it is preferred that the core comprises vegetable lipid and preferably comprises at least 90 wt. % triglycerides and more preferably essentially consists of triglycerides. The coating preferably comprises phospholipids and optionally other polar lipids. Not all polar lipids that are preferably present in the composition need necessarily be comprised in the coating, but preferably a major part is. Preferably more than 50 wt. %, more preferably more than 70 wt, %, even more preferably more than 85 wt. %, most preferably more than 95 wt. % of the polar lipids that are present in the composition are comprised in the coating of lipid globules. Not all vegetable lipids that are preferably present in the composition need necessarily be comprised in the core of lipid globules, but preferably a major part is, preferably more than 50 wt. %, more preferably more than 70 wt. %, even more preferably more than 85 wt. %, even more preferably more than 95 wt. %, most preferably more than 98 wt. % of the vegetable lipids that are present in the composition are comprised in the core of lipid globules.

The present nutritional composition preferably comprises glycerophospholipids. Glycerophospholipids are a class of lipids formed from fatty acids esterified at the hydroxyl groups on carbon-1 and carbon-2 of the backbone glycerol moiety and a negatively-charged phosphate group attached to carbon-3 of the glycerol via an ester bond, and optionally a choline group (in case of phosphatidylcholine, PC), a serine group (in case of phosphatidylserine, PS), an ethanolamine group (in case of phosphatidylethanolamine, PE), an inositol group (in case of phosphatidylinositol, PI) or a glycerol group (in case of phosphatidylglycerol, PG) attached to the phosphate group. Lysophospholipids are a class of phospholipids with one fatty acyl chain. Preferably the present composition contains PC, PS, PI and/or PE, more preferably at least PC. Preferably the glycerophospholipids comprise negatively charged phospholipids in particular PS and/or PI. Negatively charged glycerophospholipids advantageously improve the stability of the oil in water emulsion.

The present nutritional composition preferably comprises glycosphingolipids. The term glycosphingolipids as in the present invention particularly refers to glycolipids with an amino alcohol sphingosine. The sphingosine backbone is O-linked to a charged headgroup such as ethanolamine, serine or choline backbone. The backbone is also amide linked to a fatty acyl group. Glycosphingolipids are ceramides with one or more sugar residues joined in a β-glycosidic linkage at the 1-hydroxyl position. Preferably the present composition contains gangliosides, more preferably at least one ganglioside selected from the group consisting of GM3 and GD3.

The present nutritional composition preferably comprises sphingomyelin. Sphingomyelins have a phosphorylcholine or phosphorylethanolamine molecule esterified to the 1-hydroxy group of a ceramide. They are classified as phospholipid as well as sphingolipid, but are not classified as a glycerophospholipid nor as a glycosphingolipid. Sphingolipids are in the context of the present invention defined as the sum of sphingomyelin and glycosphingolipids, and phospholipids as the sum of sphingomyelin and glycerophospholipids. Preferably, the phospholipids are derived from milk lipids. Preferably the weight ratio of phospholipids:glycosphingolipids is from 2:1 to 10:1, more preferably 2:1 to 5:1.

Preferably, the present nutritional composition comprises at least 0.5 wt. % phospholipids, based on total lipid. Preferably, the nutritional composition comprises 0.5 to 20 wt. % phospholipids based on total lipid, more preferably 0.6 to 20 wt. % phospholipids based on total lipid, more preferably 0.75 to 10 wt. %, more preferably 1 to 10 wt. %, even more preferably 3 to 8 wt. %. Preferably, the nutritional composition comprises 0.1 to 10 wt. % glycosphingolipids based on total lipid, more preferably 0.5 to 5 wt. %, even more preferably 2 to 4 wt. %. Preferably, the nutritional composition comprises 0.3 to 20 wt. % (glycosphingolipids plus phospholipids) based on total lipid, more preferably 0.5 to 20 wt. % (glycosphingolipids plus phospholipids) based on total lipid, more preferably 1 to 10 wt. %.

The present nutritional composition preferably comprises cholesterol. The present composition preferably comprises at least 0.005 wt. % cholesterol based on total lipid, more preferably at least 0.02 wt. %, more preferably at least 0.05 wt. %, even more preferably at least 0.1 wt. %. Preferably the amount of cholesterol does not exceed 10 wt. % based on total lipid, more preferably does not exceed 5 wt. %, even more preferably does not exceed 1 wt. % of total lipid.

Preferably, the present composition comprises 0.5 to 25 wt. % polar lipids based on total lipid, wherein the polar lipids are the sum of phospholipids, glycosphingolipids, and cholesterol, more preferably 0.6 to 25 wt. % polar lipids based on total lipid, more preferably 0.6 to 12 wt. %, more preferably 1 to 10 wt. %, even more preferably 3 to 10 wt. %.

Preferably, the present nutritional composition comprises a lipid source selected from egg lipids, soy lecithin, sunflower lecithin, milk fat, buttermilk fat and butter serum fat (such as beta serum fat), more preferably at least egg lipid, as those are sources of phospholipids, glycosphingolipids and/or cholesterol. A preferred source for phospholipids, particularly PC, is soy lecithin and/or sunflower lecithin. The present composition preferably comprises phospholipids derived from milk. Preferably the present composition comprises phospholipids and glycosphingolipids derived from milk. Preferably also cholesterol is obtained from milk. Preferably the polar lipids are derived from milk. Polar lipids derived from milk include the polar lipids isolated from milk lipid, cream lipid, butter serum lipid (beta serum lipid), whey lipid, cheese lipid and/or buttermilk lipid. The buttermilk lipid is typically obtained during the manufacture of buttermilk. The butter serum lipid or beta serum lipid is typically obtained during the manufacture of anhydrous milk fat from butter.

Preferably the phospholipids, glycosphingolipids and/or cholesterol are obtained from milk cream. The composition preferably comprises phospholipids, glycosphingolipids and/or cholesterol from milk of cows, mares, sheep, goats, buffalos, horses and camels. It is most preferred to use a lipid extract isolated from cow's milk. Polar lipids derived from fat milk advantageously decrease adipose tissue mass to a larger extent than polar lipids from other sources. Preferably the polar lipids are located on the surface of the lipid globule, i.e. as a coating or outer layer. A suitable way to determine whether the polar lipids are located on the surface of the lipid globules is laser scanning microscopy. The concomitant use of polar lipids derived from domestic animals milk and trigycerides derived from vegetable lipids therefore enables to manufacture lipid globules with an architecture more similar to human milk, while at the same time providing an optimal fatty acid profile. Suitable commercially available sources for milk polar lipids are BAEF, SM2, SM3 and SM4 powder of Corman, Salibra of Glanbia, and LacProdan MFGM-10 or PL20 from Arla.

Preferably the source of milk polar lipids comprises at least 4 wt. % phospholipids based on total lipid, more preferably 7 to 75 wt. %, most preferably 20 to 70 wt. % phospholipids based on total lipid.

Preferably the weight ratio phospholipids to protein is above 0.10, more preferably above 0.20, even more preferably above 0.3. Preferably at least 25 wt. %, more preferably at least 40 wt. %, most preferably at least 75 wt. % of the polar lipids is derived from milk polar lipids.

Fatty Acid Composition

Herein LA refers to linoleic acid and/or acyl chain (18:2 n6); ALA refers to α-linolenic acid and/or acyl chain (18:3 n3); PUFA refers to polyunsaturated fatty acids and/or acyl chains; MUFA refers to monounsaturated fatty acids and/or acyl chains; LC-PUFA refers to long chain polyunsaturated fatty acids and/or acyl chains comprising at least 20 carbon atoms in the fatty acyl chain and with 2 or more unsaturated bonds; DHA refers to docosahexaenoic acid and/or acyl chain (22:6, n3); EPA refers to eicosapentaenoic acid and/or acyl chain (20:5 n3); ARA refers to arachidonic acid and/or acyl chain (20:4 n6); DPA refers to docosapentaenoic acid and/or acyl chain (22:5 n3). Medium chain fatty acids (MCFAs) refer to fatty acids and/or acyl chains with a chain length of 6, 8 or 10 carbon atoms.

The lipid that is present in the nutritional composition according to the invention preferably comprises PUFAs, more preferably LC-PUFAs, as LC-PUFAs further improve the growth patterns and body composition during catch-up growth, as well as brain and retina development. The nutritional composition preferably comprises 5 to 35 wt. % PUFA, more preferably 10-30 wt. % PUFA, most preferably 15-20 wt. % PUFA, based on total lipid. It is also preferred that the present nutritional composition comprises MUFAs, preferably 10 to 80 wt. % MUFA, more preferably 20-70 wt. % MUFA, most preferably 35-55 wt. % MUFA, based on total lipid.

LA preferably is present in a sufficient amount in order to promote a healthy (catch-up) growth and development, yet in an amount as low as possible to prevent occurrence of obesity later in life. The nutritional composition therefore preferably comprises less than 20 wt. % LA based on total lipid, preferably 5 to 16 wt. %, more preferably 10 to 14.5 wt. %. Preferably, the nutritional composition comprises at least 5 wt. % LA based on total lipid. Per 100 kcal, the nutritional composition preferably comprises 350-1400 mg LA. Preferably, ALA is present in a sufficient amount to promote a (catch-up) healthy growth and development of the infant. The present composition therefore preferably comprises at least 1.0 wt. % ALA based on total lipid. Preferably the composition comprises at least 1.5 wt. % ALA based on total lipid, more preferably at least 2.0 wt. %. Preferably the composition comprises less than 12.5 wt. % ALA, more preferably less than 10.0 wt. %, most preferably less than 5.0 wt. %. In case the present nutritional composition is a preterm formula or a low birthweight formula, it is preferred that the nutritional composition comprises less than 120 mg ALA, more preferably 60 to 100 mg per 100 kcal. In case the present nutritional composition is a paediatric formula for catch-up growth, it is preferred that the nutritional composition comprises less than 200 mg ALA, more preferably 100 to 150 mg per 100 kcal. In case the present nutritional composition is a preterm formula or a low birthweight formula, it is preferred that the nutritional composition comprises less than 100 mg ALA, more preferably 60 to 80 mg per 100 ml. In case the present nutritional composition is a paediatric formula for catch-up growth, it is preferred that the nutritional composition comprises less than 200 mg ALA, more preferably 130 to 150 mg per 100 ml. The weight ratio LA/ALA should be well balanced in order to prevent obesity, while at the same time ensuring a normal growth and development. Therefore, the present composition preferably comprises a weight ratio of LA/ALA between 2 and 15, more preferably between 4 and 13, even more preferably between 5 and 8. In case the present nutritional composition is a paediatric formula for catch-up growth, it is preferred that the weight ratio of LA/ALA is between 4 and 10, more preferably between 5.5 and 8.0. In case the present nutritional composition is a preterm formula or a low birthweight formula, it is preferred that the weight ratio of LA/ALA is between 4 and 10, more preferably between 5 and 8, even more preferably between 6 and 7.5, even more preferably between 6.5 and 7.5.

Since MCFA may contribute to a reduced risk of developing obesity when administered to an infant, the present composition preferably comprises at least 3 wt. % MCFA based on total lipid, more preferably at least 9 wt. %, even more preferably 15 wt. %. Since MCFA reduces adipose tissue deposition with no preference for visceral adipose tissue mass, and since MCFA does not decrease the number of adipocytes, the present composition advantageously comprises less than 50 wt. % MCFA based on total lipid, more preferably less than 40 wt. %, even more preferably less than 25 wt. %.

Preferably the present nutritional composition comprises n-3 LC-PUFA, since n-3 LC-PUFA reduce the risk of developing obesity later in life, more preferably central obesity. More preferably, the present nutritional composition comprises EPA, DPA and/or DHA, even more preferably at least DHA. Since a low concentration of DHA, DPA and/or EPA is already effective and normal growth and development are important, the content of n-3 LC-PUFA in the nutritional composition, preferably does not exceed 15 wt. % of total lipid, preferably does not exceed 10 wt. %, even more preferably does not exceed 5 wt. %. Preferably, the nutritional composition comprises at least 0.2 wt. %, preferably at least 0.5 wt. %, more preferably at least 0.75 wt. %, n-3 LC-PUFA of total lipid. The nutritional composition preferably comprises 0.05-0.7 wt. %, more preferably 0.15-0.6 wt. %, even more preferably 0.25-0.5 wt. %, even more preferably 0.3-0.5 wt. %, most preferably 0.3-0.4 wt. % DHA based on total lipid. Per 100 kcal, the nutritional composition preferably comprises 5-27 mg DHA, more preferably 10-20 mg DHA. Per 100 ml, the nutritional composition preferably comprises 8-30 mg DHA, more preferably 10-22 mg DHA, most preferably 12-19 mg DHA. The weight ratio of EPA to DHA is preferably at most 0.3, more preferably between 0.01 and 0.25.

The n-6 LC-PUFA content preferably does not exceed 5 wt. %, more preferably does not exceed 2.0 wt. %, more preferably does not exceed 0.75 wt. %, based on total lipid. Since ARA is important in infants for optimal functional membranes, especially membranes of neurological tissues, the amount of n-6 LC-PUFA is preferably at least 0.02 wt. % more preferably at least 0.05 wt. %, more preferably at least 0.1 wt. % based on total lipid, more preferably at least 0.2 wt. %. The presence of ARA is beneficial in nutrition to be administered to infants below the age of 6 months, since for these infants the infant formulae is generally the only source of nutrition. The nutritional composition preferably comprises 0.05-1.0 wt. %, more preferably 0.2-0.7 wt. %, even more preferably 0.3-0.7 wt. %, most preferably 0.3-0.5 wt. % ARA based on lipid. Per 100 kcal, the nutritional composition preferably comprises 14-27 mg ARA, more preferably 16-24 mg ARA. The weight ratio of DHA:ARA is preferably from 1:0.9 to 1:2.5, more preferably 1:1 to 1:1.9, most preferably 1:1 to 1:1.4. Per 100 ml, the nutritional composition preferably comprises 8-30 mg ARA, more preferably 12-22 mg ARA, most preferably 16-19 mg ARA. The weight ratio of DHA:ARA is preferably from 1:0.9 to 1:2.5, more preferably 1:1 to 1:1.9, most preferably 1:1 to 1:1.4.

Preferably, the nutritional composition comprises at least one source of vegetable lipid selected from sunflower oil, rapeseed oil, coconut oil and palm oil. Furthermore, it is preferred that in addition to the vegetable lipid, at least one lipid source selected from fish oil (preferably tuna fish oil), single cell oil (such as algal, microbial oil and fungal oil), MCT oil and egg lipid is present. These sources of oil are suitable as LC-PUFA sources. Preferably as a source of n-3 LC-PUFA single cell oil, including algal oil and microbial oil, is used. In a preferred embodiment the nutritional composition comprises at least one lipid selected from the group consisting of sunflower oil, rapeseed oil, coconut oil, palm oil, MCT oil, egg lipid, soy lecithin, sunflower lecithin, milk fat, buttermilk fat, butter serum fat, fish oil, marine oil, algal oil, fungal oil and microbial oil.

In an especially preferred embodiment, the nutritional composition comprises lipid in the form of lipid globules, wherein the lipid comprises, based on total lipid:
  0.5 to 25 wt. % polar lipids, preferably 0.6 to 25 wt. %, more preferably 0.6 to 12 wt. %, more preferably 1 to 10 wt. %, even more preferably 3 to 10 wt. % polar lipids,
    wherein the polar lipids comprise, based on total lipid:
      0.5 to 20 wt. % phospholipids, preferably 0.6 to 20 wt. %, more preferably 0.75 to 10 wt. %, even more preferably 1 to 10 wt. %, most preferably 3 to 8 wt. % phospholipids;
      0.1 to 10 wt. % glycosphingolipids, preferably 0.5 to 5 wt. %, more preferably 2 to 4 wt. % glycosphingolipids;
      at least 0.005 wt. % cholesterol, preferably 0.02 to 10 wt. %, more preferably 0.05 to 5 wt. %, most preferably 0.1 to 1 wt. % cholesterol;
  10 to 80 wt. % MUFA, preferably 20 to 70 wt. %, more preferably 35 to 55 wt. %;
  5 to 35 wt. % PUFA, preferably 10 to 30 wt. %, more preferably 15 to 20 wt. %;
  3 to 50 wt. % MCFA, preferably 9 to 40 wt. %, more preferably 15 to 25 wt. %;
  less than 20 wt. % LA, preferably 5 to 16 wt. %, more preferably 10 to 14.5 wt. %;
  1.0 to 12.5 wt. % ALA, preferably 1.5 to 10.0 wt. %, more preferably 2.0 to 5.0 wt %;
  0.05 to 0.7 wt. % DHA, preferably 0.15 to 0.6 wt. %, more preferably 0.3 to 0.5 wt %, even more preferably 0.25 to 0.5 wt %, most preferably 0.3 to 0.4 wt %;
  0.05 to 1.0 wt. % ARA, preferably 0.2 to 0.7 wt. %, more preferably 0.3 to 0.7 wt %, most preferably 0.3 to 0.5 wt %.

Preferably, the lipid globules have a coating comprising the major part of the polar lipids and a core comprising the major part of the other lipid components.

Process for Obtaining Lipid Globules

The present nutritional composition comprises lipid globules. The lipid globule size can be manipulated by adjusting the process steps by which the composition is manufactured. A suitable and preferred way to obtain larger lipid globule sizes is to adapt the process of homogenization such as described in WO 2010/027258. In particular aqueous and lipid phases are mixed in a batch mixer after which homogenization at a lower pressure than usually applied in the preparation of infant formula is carried out.

Alternatively, nutritional compositions having the desired lipid globule size can be prepared by the method as described in WO 2013/135738, i.e. by admixing lipid employing an inline mixer to obtain lipid globules, preferably followed by spray drying with an atomization system employing a two-fluid nozzle.

Nutritional Composition

The present nutritional composition comprises lipid and preferably further comprises protein and carbohydrates, wherein the lipids are present in lipid globules. Preferably, the nutritional composition is an infant formula, more preferably a preterm or low birthweight infant formula or paediatric formula for catch-up growth, which is intended for providing nutrition to an infant selected from the group consisting of preterm infants, small for gestational age infants and infants with retarded growth due to physical or mental stress after birth.

In view of this target group, the present nutritional composition preferably has a increased caloric density, compared to regular infant formulae, which supports growth and development of preterm infants, small for gestational age infants and infants with retarded growth due to physical or mental stress after birth. Preterm infants and small for gestational age infants usually have a little stomach and cannot consume a large amount of nutrition. Preferably, the nutritional composition contains 50 to 200 kcal/100 ml liquid, more preferably 70 to 120 kcal per 100 ml, more preferably 70 to 100 kcal per 100 ml, even more preferably 74 to 90 kcal per 100 ml, most preferably 77 to 87 kcal per 100 ml. These caloric densities are especially preferred for preterm formulae and low birthweigth formulae. For a paediatric formula for catch-up growth, the caloric density may be even higher, such as 75 to 150 kcal per 100 ml, preferably 85 to 150 kcal per 100 ml, more preferably 93 to 125 kcal per 100 ml, most preferably 95 to 115 kcal per 100 ml. The osmolarity of the nutritional composition is preferably between 150 and 420 mOsmol/l, more preferably 260 to 380 mOsm/l, even more preferably 280 to 350 mOsm/l. Such an osmolarity is beneficial in the prevention of gastrointestinal stress and ensures proper hydration, which is of importance especially for preterm and SGA infants.

Apart from the lipid, as described above, the nutritional composition according to the invention preferably comprises protein and carbohydrate.

Preferably, the protein provides 5 to 20% of the total calories of the nutritional composition, preferably 8 to 16%, more preferably 9 to 14%, more preferably 9.5 to 11.5%. In case the nutritional composition is especially designed for infants with a body weight below 1000 g, the protein content is preferably 12.5 to 14% based on total calories. It is preferred that the nutritional composition comprises 2.1 to 4.1 g protein based on 100 kcal, more preferably 2.4 to 3.4 g per 100 kcal. In case the present nutritional composition is a preterm formula or a low birthweight formula, it is preferred that the composition comprises 2.6 to 3.4 g protein based on 100 kcal. In case the nutritional composition is especially designed for infants with a body weight below 1000 g, the protein content is preferably 3.0 to 3.4 g per 100 kcal. In case the nutritional composition is especially designed for infants with a body weight above 1000 g, the protein content is preferably 2.6 to 3.0 g per 100 kcal. In case the present nutritional composition is a paediatric formula for catch-up growth, it is preferred that the composition comprises 2.4 to 2.8 g protein based on 100 kcal. Based on dry weight of the nutritional composition, the amount of protein is preferably 8 to 27 wt. %, more preferably 10 to 25 wt. %, even more preferably 13-22 wt. %. In case the present nutritional composition is a preterm formula or a low birthweight formula, it is preferred that the composition comprises 12.5 to 20 wt. % protein, more preferably 13 to 17 wt. %. In case the present nutritional composition is a paediatric formula for catch-up growth, it is preferred that the composition comprises 12.5 to 18 wt. % protein, more preferably 13 to 15 wt. %. Based on 100 ml composition, the amount of protein is preferably 1.5 to 3.3 g, more preferably 1.7 to 3.1 g, most preferably 1.9 to 2.7 g.

The source of the protein is preferably selected in such a way that the minimum requirements for essential amino acid content are met and satisfactory growth is ensured. Hence, the source of protein is preferably from bovine milk protein. Preferably, the protein component comprises whey protein and/or casein, more preferably consists of whey protein and/or casein, most preferably is a mixture of whey protein and casein. Preferably, the weight ratio of whey protein: casein is 70:30 to 40:60, more preferably 65:35 to 50:50, most preferably about 60:40. As such, an optimal amino acid profile is obtained, closely resembling that of human milk, which is beneficial for optimal catch-up growth.

The protein component may contain intact protein, partially hydrolyzed protein or free amino acids (i.e. fully hydrolyzed), preferably the protein is partially or fully hydrolyzed, as this improves the digestion of protein in SGA and premature infants.

Preferably, the carbohydrate comprises digestible carbohydrates. The digestible carbohydrates preferably provide 30 to 80% of the total calories of the nutritional composition, preferably 35 to 50%, more preferably 38 to 45%. It is preferred that the nutritional composition comprises 10 to 12 g digestible carbohydrates based on 100 kcal, preferably 10.2 to 11 g. Based on dry weight of the nutritional composition, the amount of digestible carbohydrates is preferably 20 to 80 wt. %, more preferably 40 to 65 wt. %. Based on 100 ml composition, the amount of digestible carbohydrates is preferably 3.0 to 30 g, more preferably 6.0 to 20 g, even more preferably 7.0 to 11 g per 100 ml. In case the present nutritional composition is a preterm formula or a low birthweight formula, it is preferred that the composition comprises 7.0 to 9.0 g digestible carbohydrates per 100 ml. In case the present nutritional composition is a paediatric formula for catch-up growth, it is preferred that the composition comprises 9.0 to 11 g digestible carbohydrates per 100 ml.

Preferred digestible carbohydrate sources are lactose, glucose, sucrose, fructose, galactose, maltose, starch and maltodextrin, more preferably at least lactose is present, most preferably at least lactose and starch are present. Lactose is the main digestible carbohydrate present in human milk, thus the nutritional composition preferably comprises lactose. The nutritional composition preferably comprises digestible carbohydrate, wherein at least 35 wt. %, more preferably at least 50 wt. % of the digestible carbohydrate is lactose. Based on dry weight the present composition preferably comprises at least 25 wt. % lactose.

Preferably, the carbohydrate also comprises non-digestible carbohydrates, also referred to as non-digestible oligosaccharides in the context of the present invention. Preferably the present composition comprises non-digestible oligosaccharides with a degree of polymerization (DP) of 2 to 250, more preferably 3 to 60. The non-digestible oligosaccharides advantageously prevent the onset of insulin resistance, which also may result in a reduced adipose tissue mass.

Preferably the non-digestible oligosaccharide comprises at least one oligosaccharide selected from the group of fructo-oligosaccharides (such as inulin), galacto-oligosaccharides (such as transgalacto-oligosaccharides or beta-galacto-oligisaccharides), gluco-oligosaccharides (such as gentio-, nigero- and cyclodextrin-oligosaccharides), arabino-oligosaccharides, mannan-oligosaccharides, xylo-oligosaccharides, fuco-oligosaccharides, arabinogalacto-oligosaccharides, glucomanno-oligosaccharides, galactomanno-oligosaccharides, sialic acid oligosaccharides and uronic acid oligosaccharides, more preferably selected from the group of fructo-oligosaccharides, galacto-oligosaccharides and uronic acid oligosaccharides, most preferably selected from the group of fructo-oligosaccharides, galacto-oligosaccharides. Preferably, the nutritional composition comprises galacto-oligosaccharides, more preferably transgalacto-oligosaccharides. In a preferred embodiment the composition comprises a mixture of galacto-oligosaccharides and fructo-oligosaccharides.

The galacto-oligosaccharides preferably have a DP of 2 to 10. Preferably the galacto-oligosaccharides have an average DP of below 6. The galacto-oligosaccharide is preferably selected from the group consisting of transgalacto-oligosaccharides, lacto-N-tetraose (LNT), lacto-N-neotetraose (neo-LNT), fucosyl-lactose, fucosylated LNT and fucosylated neo-LNT. Transgalacto-oligosaccharides (TOS) are for example sold under the trademark Vivinal™ (Borculo Domo Ingredients, Netherlands). Preferably the saccharides of the transgalacto-oligosaccharides are β-linked. The fructo-oligosaccharide preferably have a DP of 2 to 250, more preferably 2 to 100, most preferably 5 to 60. Preferably the fructo-oligosaccharides have an average DP of above 10. Fructo-oligosaccharides include inulin, levan and/or a mixed type of polyfructan. An especially preferred fructo-oligosaccharide is inulin. Fructo-oligosaccharide suitable for use in the compositions is commercially available, e.g. as Raftiline® HP (Orafti). Preferably, the present nutritional composition comprises galacto-oligosaccharides and fructo-oligosaccharides in a weight ratio galacto-oligosaccharides:fructo-oligosaccharides of 99:1 to 1:99, more preferably 20:1 to 1:1, most preferably 12:1 to 7:1.

Preferably, the composition comprises of 80 mg to 2 g non-digestible oligosaccharides per 100 ml, more preferably 150 mg to 1.50 g, even more preferably 300 mg to 1 g per 100 ml. Based on dry weight, the composition preferably comprises 0.25 wt. % to 20 wt. % non-digestible oligosaccharides, more preferably 0.5 wt. % to 10 wt. %, even more preferably 1.5 wt. % to 7.5 wt. % non-digestible oligosaccharides. The presence of non-digestible oligosaccharides gives rise to reduced stool viscosity and thus prevents constipation, which is particularly important in the group of vulnerable infants, such as preterm infants, SGA infants and convalescent infants.

The present nutritional composition is not human breast milk. The nutritional composition according to the invention preferably comprises other ingredients, such as minerals, trace elements, vitamins and other micronutrients as recommended and known in the art.

The nutritional composition is preferably in the form of a powder or a liquid. In one embodiment, the nutritional composition is in the form of a powder suitable for making a liquid composition after reconstitution with an aqueous solution, preferably with water. Preferably, the composition is a powder to be reconstituted with water. It was surprisingly found that the size and the coating with polar lipids of the lipid globules remained the same after the drying step and subsequent reconstitution. The presence of larger lipid globules may have a slightly negative effect on the long term stability of the liquid composition. However, separation of the lipid and aqueous layers was not observed within 48 h, which is much longer than the time between reconstituting the powder to a ready to drink liquid and the consumption of it, which will be less than 24 h and typically within 1 h. The composition being in a powder form has therefore an additional advantage in the present invention.

In case the nutritional composition is administered to an infant, it is highly preferred that the composition is in the liquid form. The preferred mode of administration is orally, e.g. bottle feeding, but other modes of administration such as tube feeding are also possible.

Preferably, the nutritional composition is in a liquid form, with a viscosity below 35 mPa·s, more preferably below 6 mPa·s, most preferably 1 to 6 mPa·s, as measured in a Brookfield viscometer at 20° C. at a shear rate of 100 s$^{-1}$. Suitably, the composition is in a powdered from, which can be reconstituted with water to form a liquid, or in a liquid concentrate form, which could be diluted with water.

In one aspect the invention relates to a nutritional composition, comprising protein, carbohydrates and lipid, wherein:
(i) the caloric density is 50 to 200 kcal per 100 ml;
(ii) lipid is present in 4.4 to 6.0 g per 100 kcal;
(iii) protein is present in 2.1 to 4.1 g per 100 kcal and in 1.5 to 3.3 g per 100 ml;
(iv) carbohydrates are present in 10 to 12 g per 100 kcal,
(v) the lipid is present in lipid globules, having:
(a) a volume-weighted mode diameter of at least 1.0 µm; and/or
(b) a phospholipid coating, wherein the composition comprises at least 0.5 wt. % phospholipids based on total lipid.

In one aspect the invention relates to a preterm formula, a low birthweight formula, comprising protein, carbohydrates and lipid, wherein:
(i) the caloric density is 77 to 87 kcal per 100 ml;
(ii) lipid is present in 4.4 to 6.0 g per 100 kcal;
(iii) protein is present in 2.6 to 3.4 g per 100 kcal and in 1.7 to 3.1 g per 100 ml;
(iv) carbohydrates are present in 10 to 12 g per 100 kcal,
(v) the lipid is present in lipid globules, having:
(a) a volume-weighted mode diameter of at least 1.0 µm; and/or
(b) a phospholipid coating, wherein the composition comprises at least 0.5 wt. % phospholipids based on total lipid.

In one aspect the invention relates to a paediatric formula for catch-up growth, comprising protein, carbohydrates and lipid, wherein:
(i) the caloric density is 93 to 125 kcal per 100 ml;
(ii) lipid is present in 4.4 to 6.0 g per 100 kcal;
(iii) protein is present in 2.4 to 2.8 g per 100 kcal and in 1.7 to 3.1 g per 100 ml;
(iv) carbohydrates are present in 10 to 12 g per 100 kcal,
(v) the lipid is present in lipid globules, having:
(a) a volume-weighted mode diameter of at least 1.0 µm; and/or
(b) a phospholipid coating, wherein the composition comprises at least 0.5 wt. % phospholipids based on total lipid.

In one embodiment, the preterm formula, low birthweight formula or paediatric formula for catch-up growth comprises 0.3 to 0.7 wt. % arachidonic acid, based on total lipid, preferably 0.4 to 0.6 wt. % arachidonic acid, based on total lipid.

In yet a further embodiment, the preterm formula, low birthweight formula or paediatric formula for catch-up growth comprises 0.3 to 0.5 wt. % docosahexaenoic acid, based on total lipid.

Application

The present composition is preferably administered orally to the infant. The present invention aims to promote controlled catch-up growth in an infant selected from the group of preterm infants, small for gestational age infants and convalescent infants. In the context of the present invention, 'controlled catch-up growth' can also be referred to as 'balanced catch up growth' or 'proportional weight for length catch up growth'. In the context of the present invention, 'uncontrolled catch-up growth or 'unbalanced catch-upgrowth or 'accelarated catch-up growth', also referred to as 'excessive weight gain', is defined as an increase in weight adjusted for length of >0.5 SD score in the first three months of life, see for example Kerkhof & Hokken-Koelega, Nat. Rev. Endocrinol. 8, 689-692 (2012); Kerkhof et al. J Clin Endocrinol Metab 97: 4498-4506, (2012). In this context, the first three months of life for preterm infants start at term age and for SGA infants at birth. For convalescent infants 'uncontrolled catch-up growth' or 'unbalanced catch-up growth' or 'accelarated catch-up growth' or 'excessive weight gain', is defined as an increase in weight adjusted for length of >0.5 SD score in the first three months from the start of recovery of the convalescent infant. Consequently, controlled catch up in the present context is defined as a weight gain adjusted for length of <0.5 SD score within three months, wherein the three months are the first three months after term age for preterms and after birth for the SGA infants, and is defined as a weight gain adjusted for length of <0.5 SD score within three months after start of recovery for convalescent infants, e.g. the first three months after the growth retardation due to mental or physical stress has stopped.

The present invention also aims to (i) improve body composition, (ii) improve adipose tissue distribution, (iii) decrease visceral adipose tissue based on body weight and/or on total adipose tissue, and/or (iv) decrease the ratio visceral adipose tissue to subcutaneous adipose tissue, in an infant selected from the group consisting of preterm infants, small for gestational age infants and convalescent infants, preferably during or directly after catch-up growth. In one embodiment the present method is for preventing visceral adiposity.

In one embodiment, the present nutritional composition is for feeding an infant selected from the group consisting of preterm infants, small for gestational age infants and convalescent infants. Such feeding preferably promotes controlled catch-up growth. Such feeding preferably (i) improves body composition, (ii) improves adipose tissue distribution, (iii) decreases visceral adipose tissue based on body weight and/or on total adipose tissue, and/or (iv) decreases the ratio visceral adipose tissue to subcutaneous adipose tissue. Preferably, these effects are observed during or directly after catch-up growth, more preferably before the infant reaches an age of 36 months, most preferably before the infant reaches an age of 12 months. This does not mean that effects cease to be observable after the infant has reached the age of 12 months or 36 months, as the beneficial effect of the present nutritional composition may prolong to later in life.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

EXAMPLES

Example 1: Process for Preparing an IMF with Larger Lipid Globule Size

An infant formula was prepared as described in example 1 of WO 2013/135738. In particular, an infant formula in the form of a powder was prepared comprising per kg final product about 4800 kcal, about 247 g lipid, about 540 g digestible carbohydrates, about 41 g non-digestible oligosaccharides and about 97 g protein. The composition was prepared using butter milk serum powder enriched in milk phospholipids, a vegetable oil blend (lipid), demineralised whey powder (protein), lactose, and non-digestible oligosaccharides. Also vitamins, minerals, trace elements as known in the art were used.

The amount of butter milk serum powder was such that 1.62 wt. % phospholipids based on total lipids were present in the final composition. An aqueous phase, comprising the butter milk powder, protein and digestible carbohydrates and the other ingredients, except the lipid and lipid soluble vitamins, was prepared as known in the art and heat treated to prevent bacterial contamination, namely by an Ultra High Temperature (UHT) treatment, as known in the art, after which an evaporation step was applied. The dry matter content of the aqueous phase was between 30 to 48 wt. % after the evaporation step. The mixture was heated to 50° C.

A lipid phase was prepared as known in the art. The vegetable oil blend was also heated to 50° C. and added to the water phase in a w/w ratio of between 15 to 30 by injection and a centrifugal booster pump. The total solid content of the lipid and aqueous phase mixture was between 40 and 60 wt. %. Accordingly, the aqueous and lipid phase were fed into the inline mixer (Ystral Z80) comprising one mixing head. The rotar stator design of the inline mixer had 3 rows of teeth. The aqueous and lipid phase were mixed with a tip speed of 20 to 50 m/s (resulting in a shear rate from 50000 to 100000/s) in order to emulsify the lipid phase into the aqueous phase and thereafter pumped with a positive displacement pump, a mono pump, with a pressure of about 8 bar to the heater.

The oil in water mixture was subsequently fed via the concentrate heater to the spray dryer, driven by the pump used downstream of the inline mixer.

The emulsion was atomized with a low shear atomization system employing a two-fluid nozzle of Schlick (0/2-0/5 series), wherein the pressure used for spray-drying was below 8 bar, and dried with the inlet temperature of the drying gas being 195° C. The size of the lipid globules in the final powder, after reconstitution with water, was measured with a Mastersizer 2000 (Malvern Instruments, Malvern UK). The volume weighted mode diameter was 4.3 µm. About 60% of the lipid globules based on lipid volume had a diameter between 2 and 12 µm.

Example 2: An Early in Life Diet with Large Lipid Globules and Milk Phospholipids Improves Catch-Up Growth in IUGR Rats Methods: Male offspring of Wistar dams either underwent prenatal bilateral uterine artery and vein operation (LIG) or a sham operation (SOP) on day 19 of the first pregnancy of the dams. Offspring of dams without treatment served as controls (C). Control diet 1 or experimental diet 2 was provided for 4 weeks between postnatal days 15 (P15) and 42 (P42).

Control and Experimental Diets were:

Diet 1: The control diet was a standard infant milk formula (IMF) based control diet. This diet comprised 282 g standard Nutrilon 1® per kg, having lipid globules with a volume weighted mode diameter of 0.4 µm, and no added polar lipids. The rest of the diet was AIN-93G protein, carbohydrates and fibre. The volume % of lipid globules with a size between 2 and 12 m was below 40% based on total lipid volume. All lipid present in the diet was derived from the IMF.

Diet 2: The experimental diet was based on the infant formula prepared according to example 1. This experimental diet differed from diet 1 in that it comprised 282 g infant formula of example 1, i.e. comprised lipid globules larger than the control coated with polar lipids derived from milk. All lipid present in the diet was derived from the IMF.

Thus, six groups were compared: (a) LIG-diet 2 (n=8); (b) SOP-diet 2 (n=10); (c) C-diet 2 (n=20); (d) LIG-diet 1 (n=9); (e) SOP-diet 1 (n=10); and (f) C-diet 1 (n=10). Accumulation of body weight was recorded weekly. Crown-rump-length and body composition were detected via micro-CT scan on P42.

All blocks were tested for outliers using Grubbs Test. Maximally 1 value per block was removed (in most blocks no outlier). All data were normally distributed. A 1 way ANOVA test was performed with a Bonferroni correction, and in case of significant a ANOVA value, a T-test was performed if the data showed a similar variance, otherwise a MW test was applied. Group comparisons were made between:

(a) LIG-diet 2 vs. (b) SOP-diet 2;
(a) LIG-diet 2 vs. (c) C-diet 2;
(b) SOP-diet 2 vs. (c) C-diet 2;
(d) LIG-diet 1 vs. (e) SOP-diet 1;
(d) LIG-diet 1 vs. (f) C-diet 1;
(e) SOP-diet 1 vs. (f) C-diet 1;
(a) LIG-diet 2 vs. (d) LIG-diet 1;
(b) SOP-diet 2 vs. (e) SOP-diet 1; and
(c) C-diet 2 vs. (f) C-diet 1.

Results: No difference in food intake was observed between the different groups. In Table 2 the body weight development over time is shown. In general, the two LIG groups showed the lowest body weight direct after birth and over time (except for LIG-diet 1 at P40), and the bodyweight of the two C groups was highest at P2, P12 and P40. So, all groups experienced a very similar rate of (catch-up) growth, irrespective of which diet was administered.

TABLE 2

Body weight development over time

| | sample size | Postnatal day (P) | | | | | |
|---|---|---|---|---|---|---|---|
| | | 2 | | 12 | | 40 | |
| Group | | BW (g) | SD | BW (g) | SD | BW (g) | SD |
| (a) LIG-diet 2 | 9 | 5.667 | 0.324 | 28.98 | 2.334 | 159.6 | 10.3 |
| (b) SOP-diet 2 | 10 | 6.19 | 0.7156 | 28.39 | 1.371 | 165.4 | 10.19 |
| (c) C-diet 2 | 20 | 7.225 * | 0.8263 | 32.1 * | 2.081 | 175.3 + | 9.603 |
| (d) LIG-diet 1 | 9 | 5.767 | 0.5148 | 28.18 | 1.295 | 164.3 | 7.07 |
| (e) SOP-diet 1 | 10 | 6.66 | 0.2271 | 30.09 | 1.38 | 162.5 | 12.02 |
| (f) C-diet 1 | 10 | 7.28 # | 0.5554 | 32.53 # | 2.091 | 174.2 | 13.71 |

BW = body weight; SD = standard deviation.
* p < 0.001 vs. LIG-diet 2 and vs. SOP-diet 2; # p < 0.001 vs. LIG-diet 1; + p < 0.01 vs. LIG-diet 2.

In Table 3, the body composition at P42 is shown. The amount of total adipose tissue mass (ATM) based on body weight was highest in the LIG-diet 1 group, when compared with the other groups. This was in particular the case for the visceral adipose tissue mass (VTM). This is indicative for the increased catch-up growth in the LIG-diet 1 group, resulting in increased adipose tissue deposition, in particular visceral adipose tissue. The amount adipose tissue mass in the LIG-diet 2 group, which were fed with a nutritional composition according to the invention, was very similar to the control (C) and SOP groups. Interestingly, the amount of visceral tissue mass, both based on body weight or total adipose tissue mass, was decreased in the LIG-diet 2 group, when compared to all other groups, and statistically significant lower than in the LIG-diet 1 group. On the other hand, subcutaneous tissue mass (STM), based on body weight and based on total adipose tissue mass, was higher in the LIG-diet 2 group than in the other two-diet 2 groups, as well as compared to the LIG-diet 1 group, which indicates that the LIG group benefits most from the nutritional composition according to the invention.

TABLE 3

Body composition at P42

| Group | BW g (SD) | ATM * wt. % (SD) | VTM * wt. % (SD) | VTM ** wt. % (SD) | STM * wt. % (SD) | STM ** wt. % (SD) |
|---|---|---|---|---|---|---|
| (a) LIG-diet 2 | 159.6 (10.3) | 2.62 (0.62) | 1.4 & (0.26) | 51.94 & (4.997) | 1.2 (0.4) | 48.06 $ (4.997) |
| (b) SOP-diet 2 | 165.4 (10.19) | 2.49 (0.58) | 1.5 (0.30) | 61.77 (8.711) | 1.0 (0.4) | 38.23 (8.711) |
| (c) C-diet 2 | 175.3 + (9.603) | 2.55 (0.54) | 1.5 (0.31) | 57.55 (6.495) | 1.1 (0.3) | 42.45 (6.495) |
| (d) LIG-diet 1 | 164.3 # (7.07) | 3.06 (0.53) | 1.8 (0.30) | 56.67 (1.584) | 1.3 (0.3) | 43.33 (1.584) |
| (e) SOP-diet 1 | 162.5 (12.02) | 2.63 (0.56) | 1.6 (0.31) | 58.76 (4.104) | 1.0 (0.3) | 41.24 (4.104) |
| (f) C-diet 1 | 174.2 (13.71) | 2.63 (0.38) | 1.6 (0.32) | 60.81 (7.525) | 1.0 (0.2) | 39.19 (7.525) |

BW = body weight; SD = standard deviation; ATM = total adipose tissue mass; VTM = visceral adipose tissue mass; STM = subcutaneous adipose tissue mass; * = in wt. %, based on BW; ** = in wt. %, based on ATM.
$p < 0.05$: + vs. LIG-diet 2 and vs. SOP-diet 2; # vs. C-diet 1; & vs. LIG-diet 1; $ vs. SOP-diet 2; C-diet 2 and vs. LIG-diet 1.

These results are indicative for the beneficial effect of the experimental diet in promoting controlled catch-up growth, as well as on improving body composition, improving adipose tissue distribution, decreasing visceral adipose tissue based on body weight and/or on total adipose tissue, and/or decreasing the ratio visceral adipose tissue to subcutaneous adipose tissue, in particular in SGA or preterm infants.

Example 3: Infant Formula for Premature or Low Birthweight Infants

A preterm or low birth weight formula comprising per 100 ml, of which 87.4 g water and 12.6 g
dry matter:
Energy: 81 kcal
Protein: 2.64 g (bovine whey protein/casein 6/4 wt/wt ratio)
Digestible carbohydrates: 8.40 (2.37 g starch, 5.73 sugars (mainly lactose))
Lipid: 3.9 g, a mix of rapeseed oil, sunflower oil, coconut oil, palm kernel oil, corn oil, single cell oil, milk fat (including polar lipids) and fish oil, with the same lipid globule architecture as in example 1 (comprising 503 mg LA, 72 mg ALA, 17.7 mg ARA, 13.6 mg DHA)
Non digestible oligosaccharides: 0.8 g (galacto-oligosaccharides (short chain—average DP below 7) and fructo-oligosaccharides (long chain—average DP above 7) in a 9/1 wt/wt ratio), representing 0.6 g fiber according to EU regulation.
Vitamins, minerals and other micronutrients according to guidelines.

Example 4: Infant Formula for Convalescent Infants

A paediatric formula comprising per 100 ml (15 wt % dry weight and 85 ml water):
Energy: 101 kcal
Protein: 2.6 g (bovine whey protein/casein 6/4 wt/wt ratio)
Digestible carbohydrates: 10.3 (4.4 g polysaccharides (mainly starch), the rest mainly sugars, of which the majority (5.2 g) is lactose)
Lipid: 5.4 g, a mix of rapeseed oil, sunflower oil, coconut oil, palm kernel oil, corn oil, single cell oil, milk fat (including polar lipids) and fish oil, with the same lipid globule architecture as in example 1 (comprising 799 mg LA, 139 mg ALA, 17.7 mg ARA, 17.6 mg DHA)
Non digestible oligosaccharides: 0.8 g (galacto-oligosaccharides (short chain—average DP below 7) and fructo-oligosaccharides (long chain—average DP above 7) in a 9/1 wt/wt ratio), representing 0.6 g fiber according to EU regulations.
Vitamins, minerals and other micronutrients according to guidelines.

The invention claimed is:

1. A method for promoting controlled catch-up growth in an infant selected from the group consisting of:
   preterm infants, defined as born before 37 weeks pregnancy of the mother;
   small for gestational age infants, defined as having a birth weight below the 10th percentile for the gestational age; and
   infants with retarded growth, wherein the retarded growth is due to physical or mental stress after birth,
the method comprising administering to the infant in need thereof a nutritional composition, comprising:
   (i) 4.4 to 6.0 g lipid per 100 kcal;
   (ii) 2.6 to 4.1 g protein per 100 kcal and 1.9 to 3.3 g per 100 ml, wherein the protein comprises casein and non-micellar whey protein sourced from bovine milk; and
   (iii) 10 to 12 g carbohydrates per 100 kcal;
wherein the nutritional composition comprises a caloric density between 95 to 115 kcal per 100 ml; and
wherein the lipid is present in lipid globules, having:
   (a) a volume-weighted mode diameter of at least 1.0 µm; and
   (b) a phospholipid coating, wherein the infant formula comprises at least 0.5 wt. % phospholipids based on total lipid;
wherein controlled catch up growth is defined as a weight gain adjusted for length of <0.5 SD score within three months, wherein the three months are the first three months after term age for preterm infants and after birth for small for gestational age infants, and is defined as a weight gain adjusted for length of <0.5 SD score within three months after start of recovery for infants with retarded growth due to physical or mental stress after birth which is the first three months after the growth retardation due to mental or physical stress has stopped.

2. The method according to claim 1, wherein the nutritional composition is selected from the group consisting of a preterm formula, a low birthweight formula, and a paediatric formula for catch-up growth.

3. The method according to claim 2, wherein the nutritional composition is a preterm formula or a low birthweight formula, comprising 2.6 to 3.4 g protein per 100 kcal and 1.9 to 3.1 g protein per 100 ml.

4. The method according to claim 1, wherein the nutritional composition is a paediatric formula for catch-up growth, comprising 2.4 to 2.8 g protein per 100 kcal and 1.7 to 3.1 g protein per 100 ml.

5. The method according to claim 1, wherein the nutritional composition comprises 0.3 to 0.7 wt. % arachidonic acid, based on total lipid.

6. The method according to claim 1, wherein the nutritional composition comprises 0.3 to 0.5 wt. % docosahexaenoic acid, based on total lipid.

7. The method according to claim 1, wherein the whey protein and casein are present in a weight ratio of 70:30 to 40:60 whey protein:casein.

8. The method according to claim 7, wherein the weight ratio of whey protein:casein is 65:35 to 50:50.

9. The method according to claim 1, wherein the protein does not comprise micellar whey protein.

10. The method according to claim 1, wherein the phospholipids comprise sphingomyelin.

11. The method according to claim 1, wherein the phospholipids are derived from milk lipids.

* * * * *